(12) United States Patent
Thayumanavan et al.

(10) Patent No.: US 11,672,867 B2
(45) Date of Patent: Jun. 13, 2023

(54) PROTEIN-TEMPLATED SELF-ASSEMBLY OF A COVALENT POLYMER NETWORK FOR INTRACELLULAR TRAFFICKING AND TRACELESS RELEASE

(71) Applicant: University of Massachusetts, Boston, MA (US)

(72) Inventors: Sankaran Thayumanavan, Amherst, MA (US); Jiaming Zhuang, Amherst, MA (US)

(73) Assignee: University of Massachusetts, Boston, MA (US)

( * ) Notice: Subject to any disclaimer, the term of this patent is extended or adjusted under 35 U.S.C. 154(b) by 319 days.

(21) Appl. No.: 16/497,145

(22) PCT Filed: Mar. 30, 2018

(86) PCT No.: PCT/US2018/025580
§ 371 (c)(1),
(2) Date: Sep. 24, 2019

(87) PCT Pub. No.: WO2018/231323
PCT Pub. Date: Dec. 20, 2018

(65) Prior Publication Data
US 2020/0282066 A1    Sep. 10, 2020

Related U.S. Application Data

(60) Provisional application No. 62/478,820, filed on Mar. 30, 2017.

(51) Int. Cl.
*A61K 47/55*     (2017.01)
*A61K 47/69*     (2017.01)
*B82Y 5/00*      (2011.01)

(52) U.S. Cl.
CPC .......... *A61K 47/55* (2017.08); *A61K 47/6931* (2017.08); *B82Y 5/00* (2013.01)

(58) Field of Classification Search
CPC ........................... A61K 47/55; A61K 47/6931
See application file for complete search history.

(56) References Cited

U.S. PATENT DOCUMENTS 3,940,542 A * 2/1976 Knopf .................... D01F 11/08
521/905

OTHER PUBLICATIONS

Matsumoto et al. "Synthesis of nanogel-protein conjugates", Polym. Chem., 2013, 4, 2464-2469 (Year: 2013).*
Topala et al. "Bovine Serum Albumin Interactions With Metal Complexes", Clujul Medical 2014 vol. 87—No. 4 (Year: 2014).*

* cited by examiner

*Primary Examiner* — James W Rogers
(74) *Attorney, Agent, or Firm* — Milstein Zhang & Wu LLC

(57) ABSTRACT

The invention provides polymers and polymer-based nano-structures, in particular, polymers and polymer network to which biomolecules (e.g., proteins, antibodies, peptide aptamers) can be covalently conjugated and stably encapsulated therein and be controllably delivered and released upon degradation of the nano-structures in response to specific microenvironment, and compositions and methods of preparation and use thereof.

7 Claims, 35 Drawing Sheets
Specification includes a Sequence Listing.

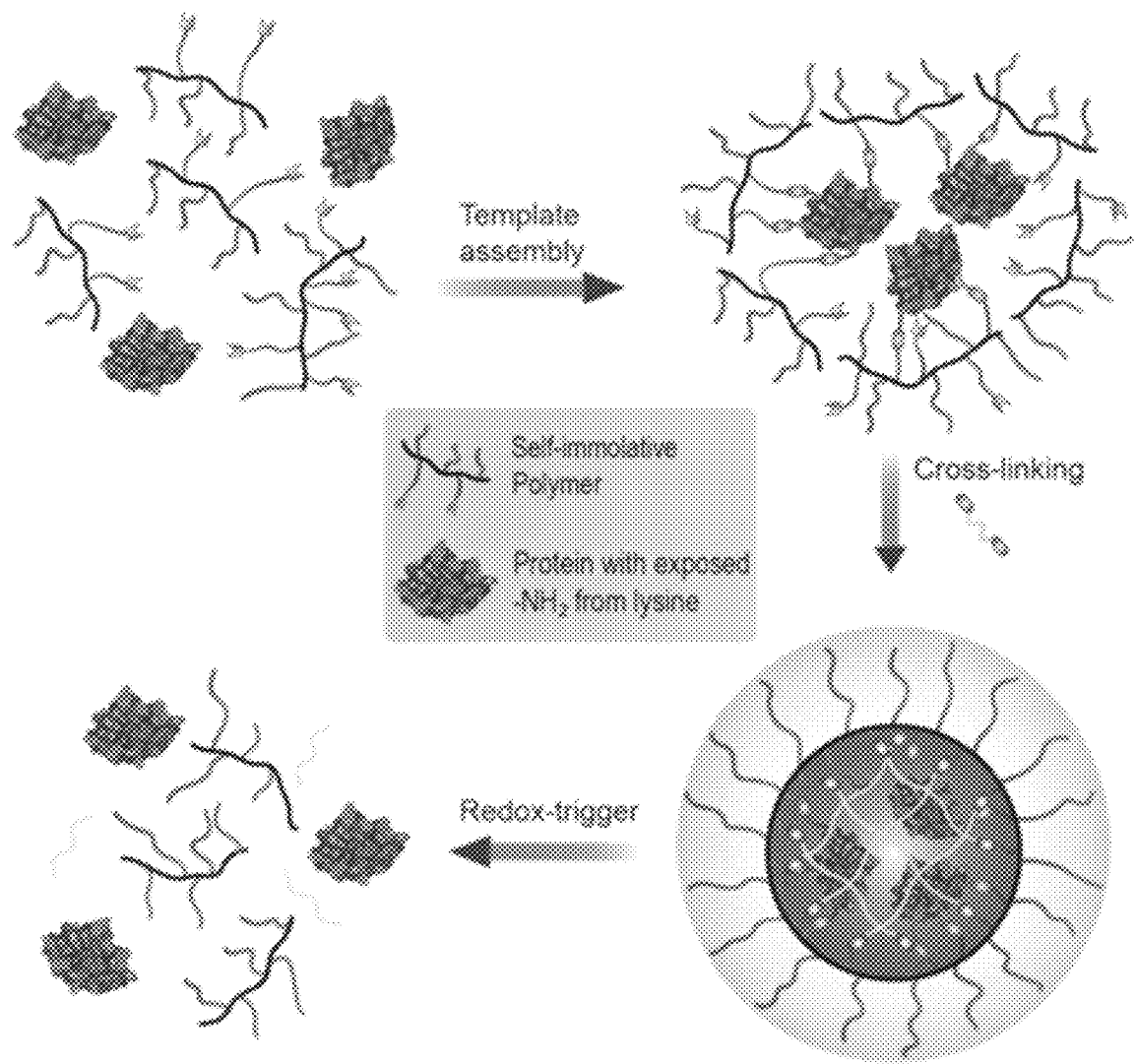
FIG. 1A. Schematic representation of the formation of a covalent polymer network using the protein as the template and its traceless and triggered release in a reducing environment.

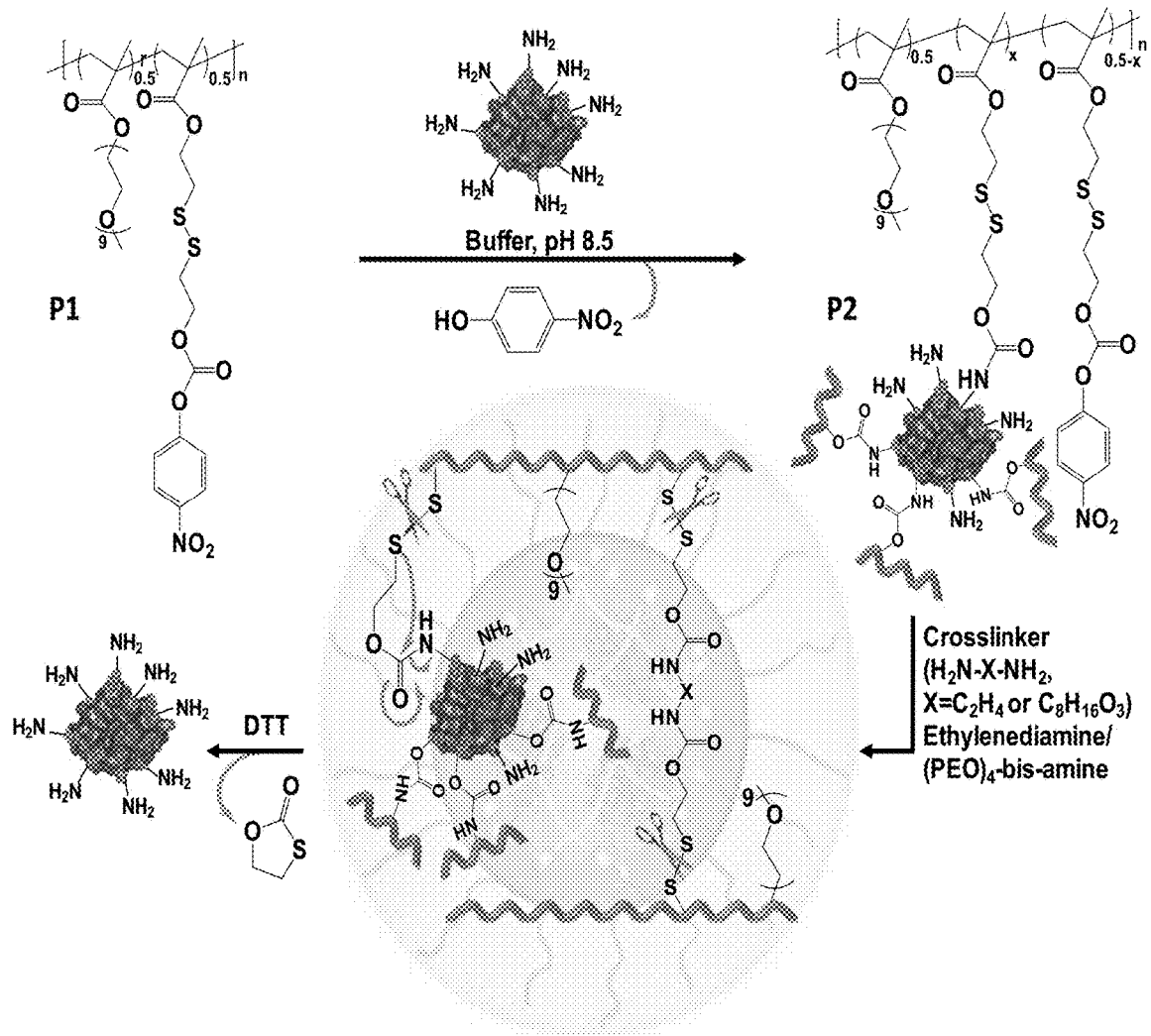
FIG. 1B. *Scheme 1.* Chemical structures of polymers and the reaction scheme for protein conjugation, crosslinking to generate the nanoassembly and its release in the presence of a reducing agent.

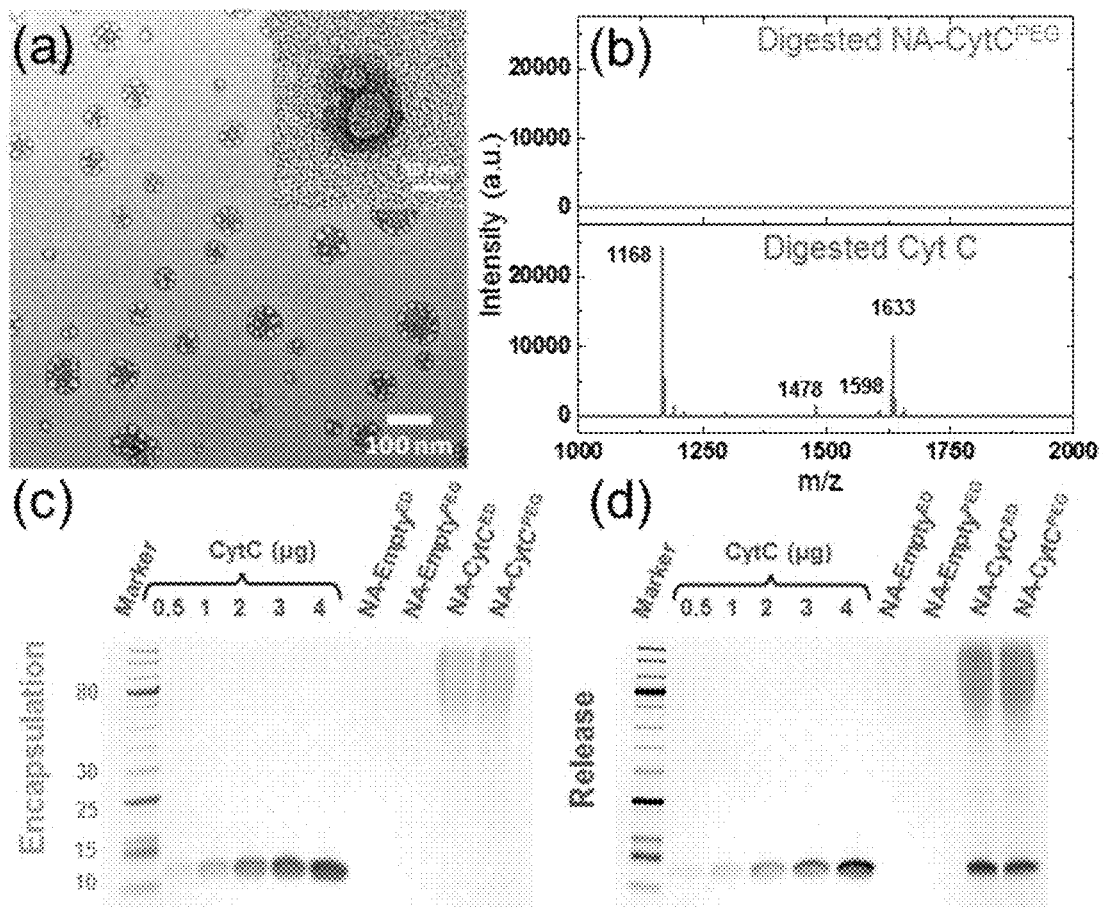
FIG. 2. (a) TEM image of the clustered NA-CytC$^{PEG}$ particles, with the zoom-in of one of the particles in the inset. (b) MALDI-MS analysis of the trypsin digest from the encapsulated and naked CytC; (c, d) SDS-PAGE of the NA-CytC$^{PEG}$ under non-reducing and reducing conditions.

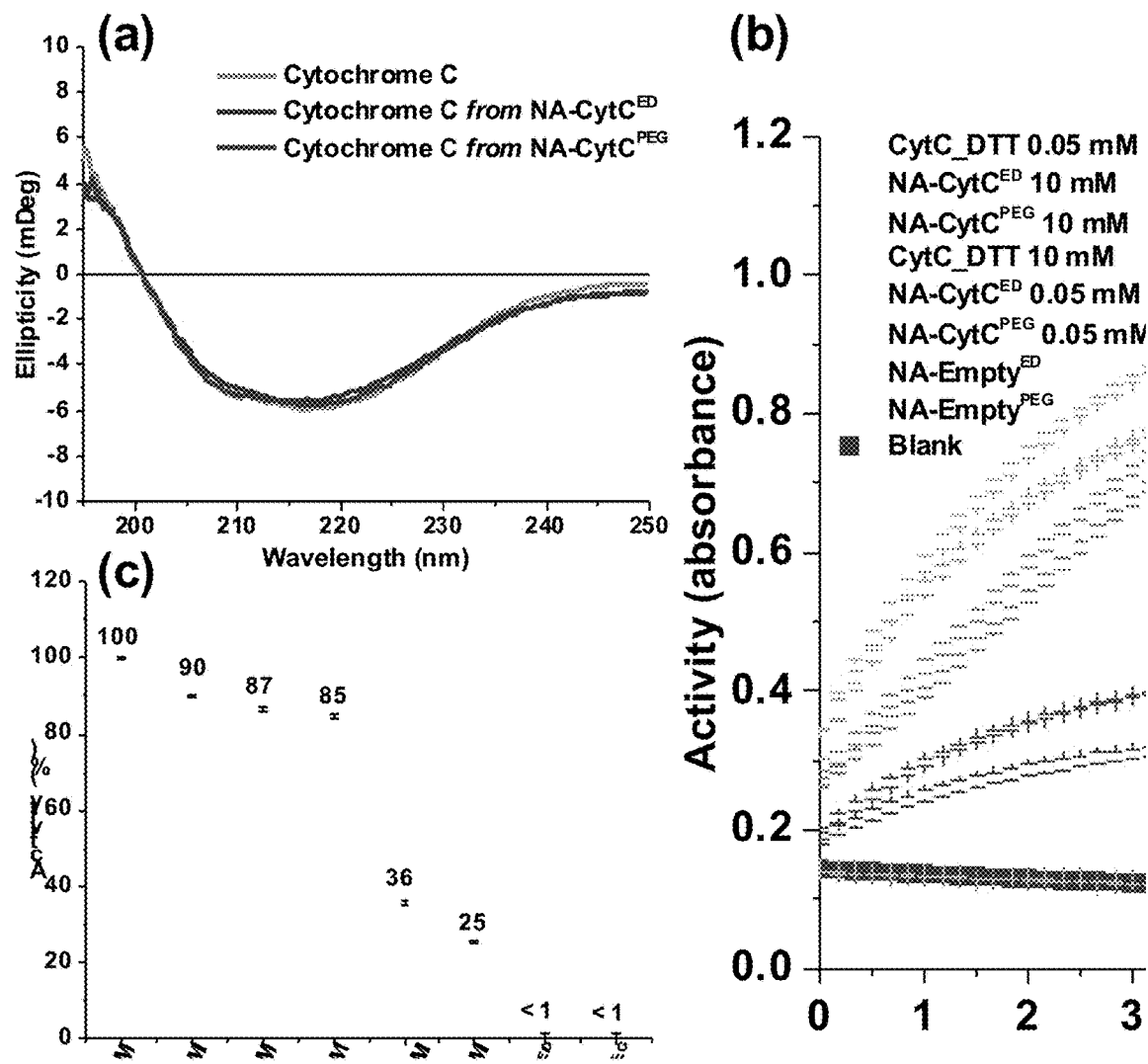
FIG. 3. Structure and function of released CytC from the NA-CytC[PEG], evaluated by (a) circular dichroism (CD); and (b-c) ABTS activity assay.

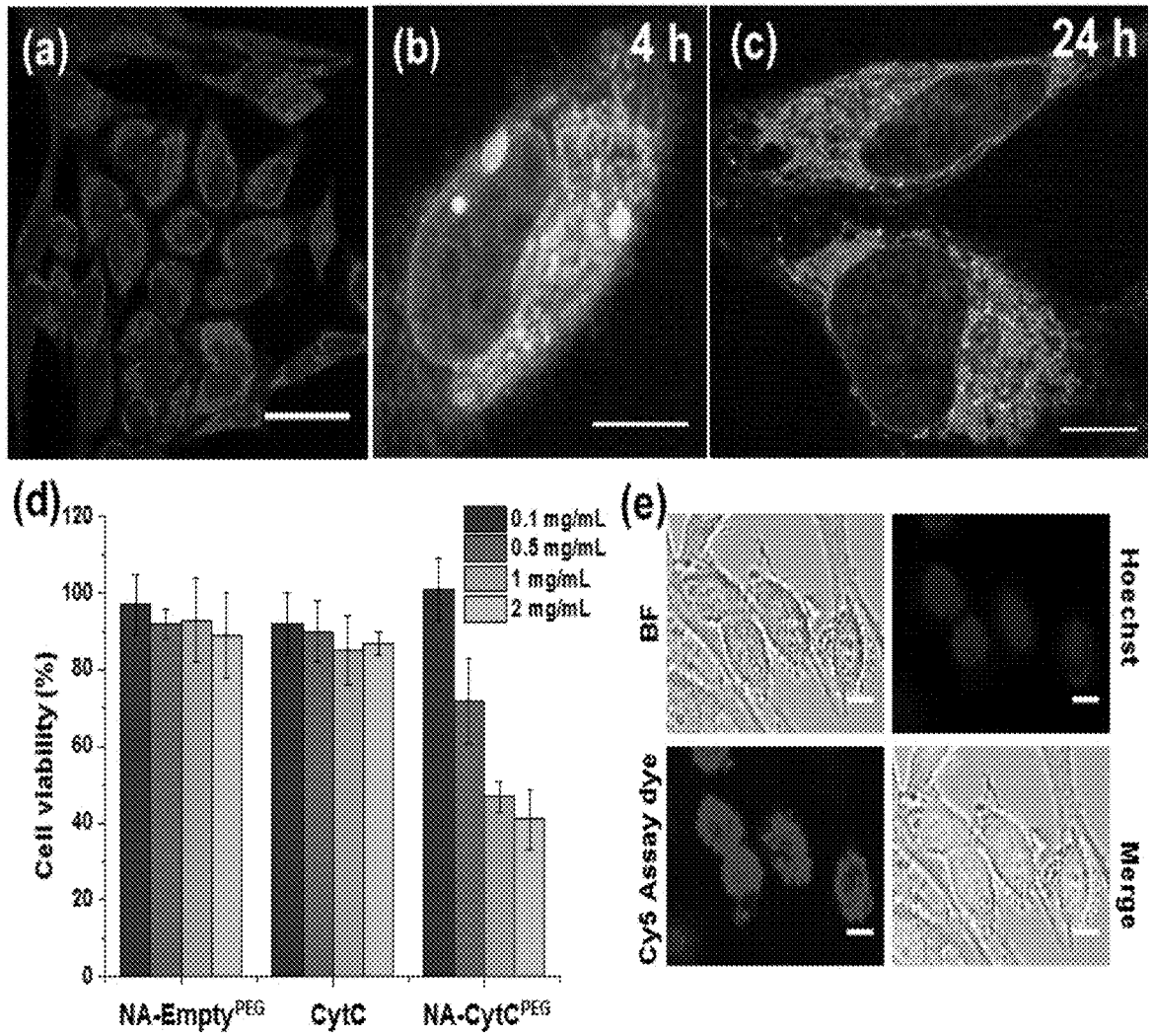
FIG. 4. HeLa cells treated with NA-CytC$^{PEG}$ conjugates to study cellular uptake: (a) 4 h post-incubation; (b-c) endosomal co-localization and escape at 4 h and 24 h, respectively; (green: lysotracker; red: rhodamine B; blue: hoechst); (d) cell viability (after 72 h); (e) detection of activated caspase-3/7 after 72 h using the Cy5 reagent; scale bar: (a) 50 μm, (b, c, e) 10 μm.

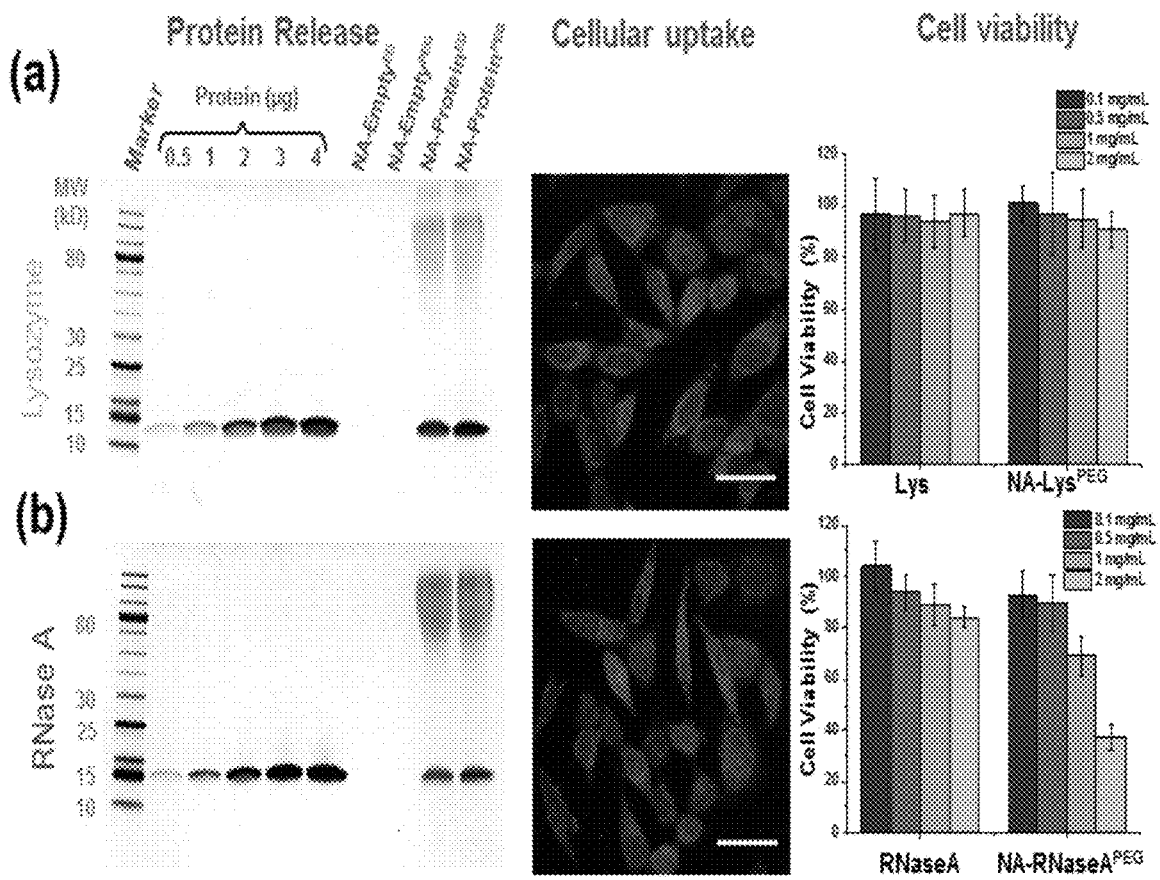
FIG. 5. SDS-PAGE showing protein release (under reducing conditions), cellular uptake (4 h) and viability (72 h) in HeLa cells for (a) NA-Lys and (b) NA-RNaseA conjugates, scale bar: 50 μm.

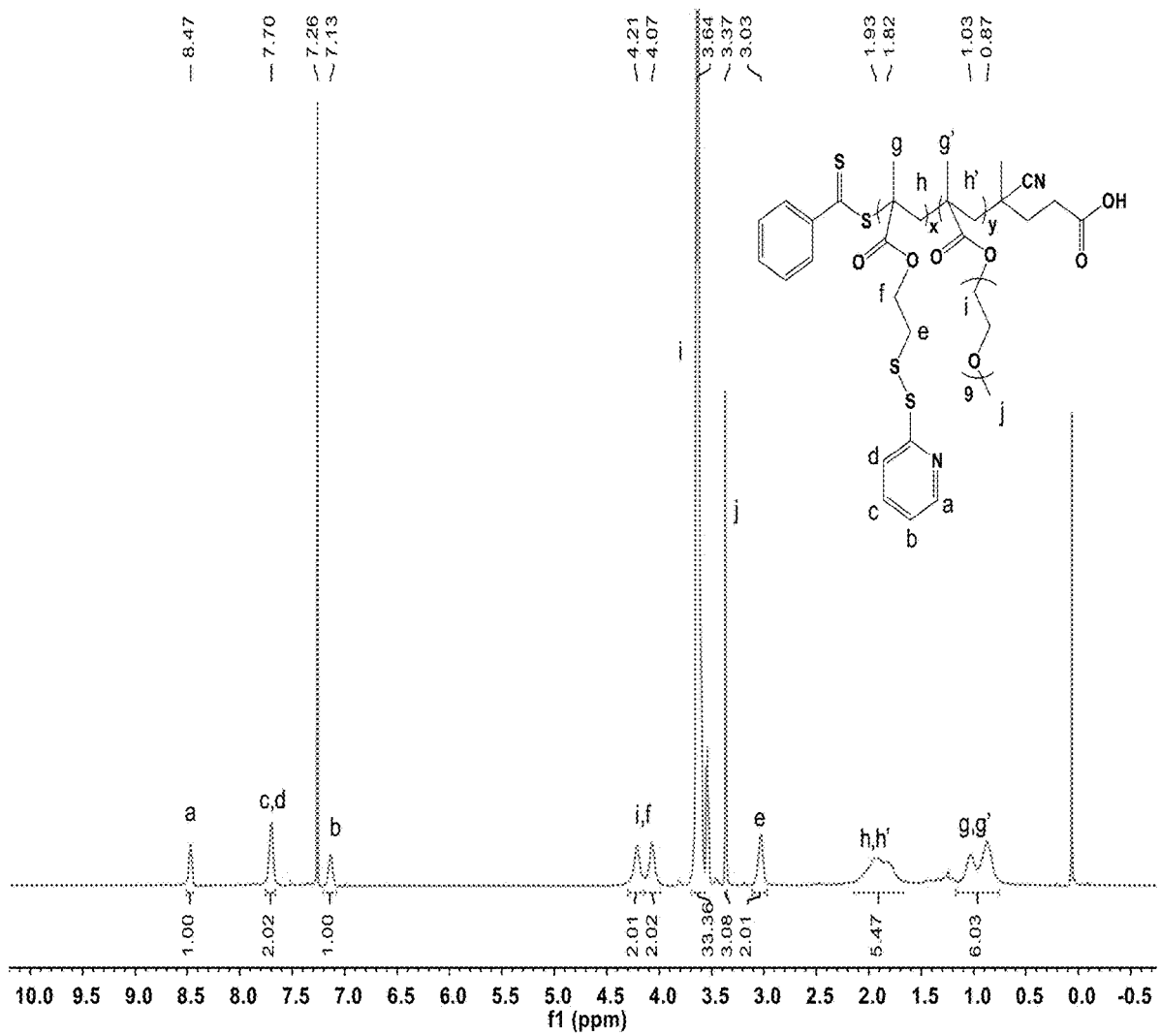
FIG. 6. $^1$H-NMR spectra of p(PEGMA-co-PDSMA), P$_{PcP}$

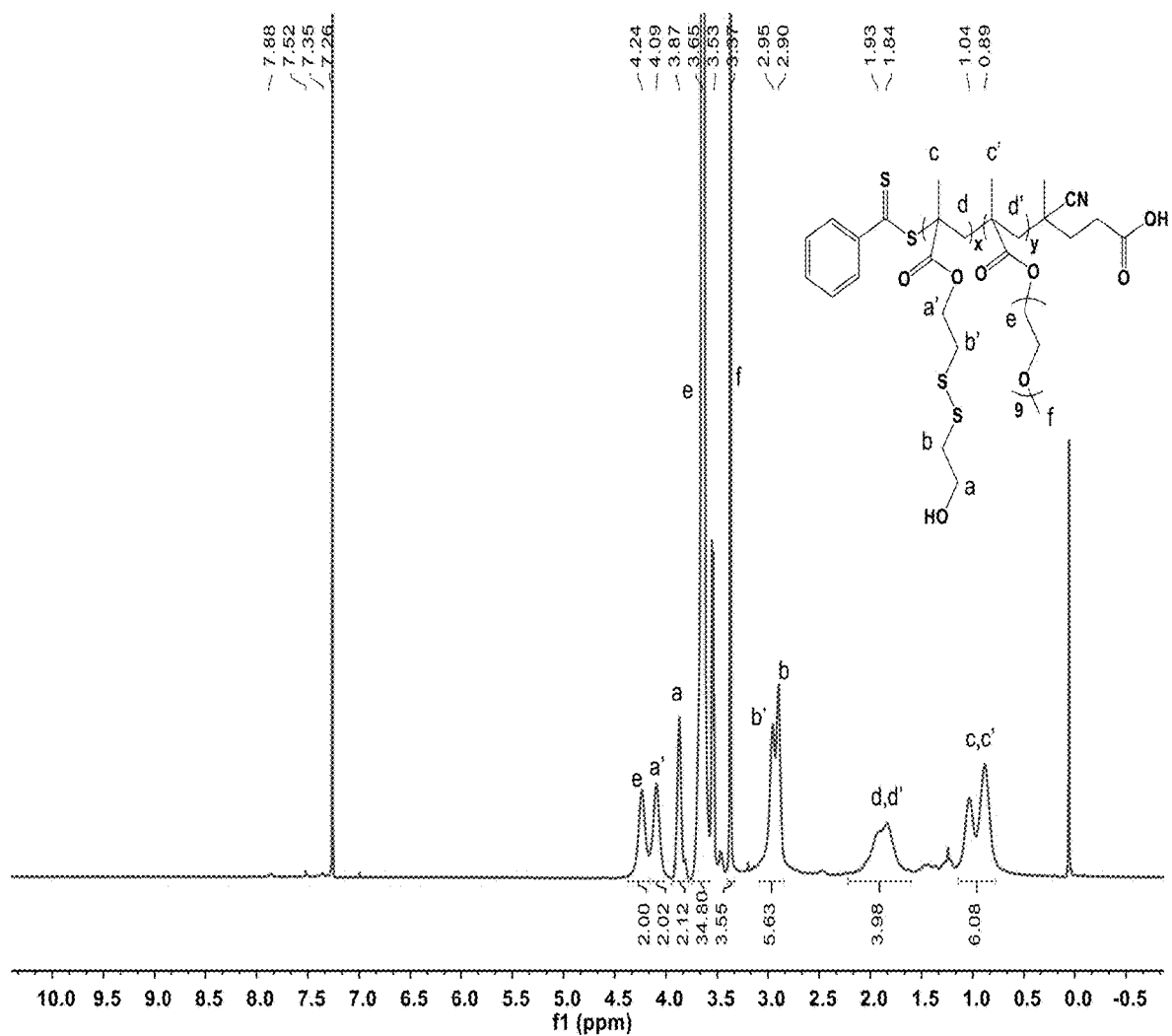
FIG. 7. ¹H-NMR spectra of p(PEGMA-co-EDSMA), P$_{PcE}$

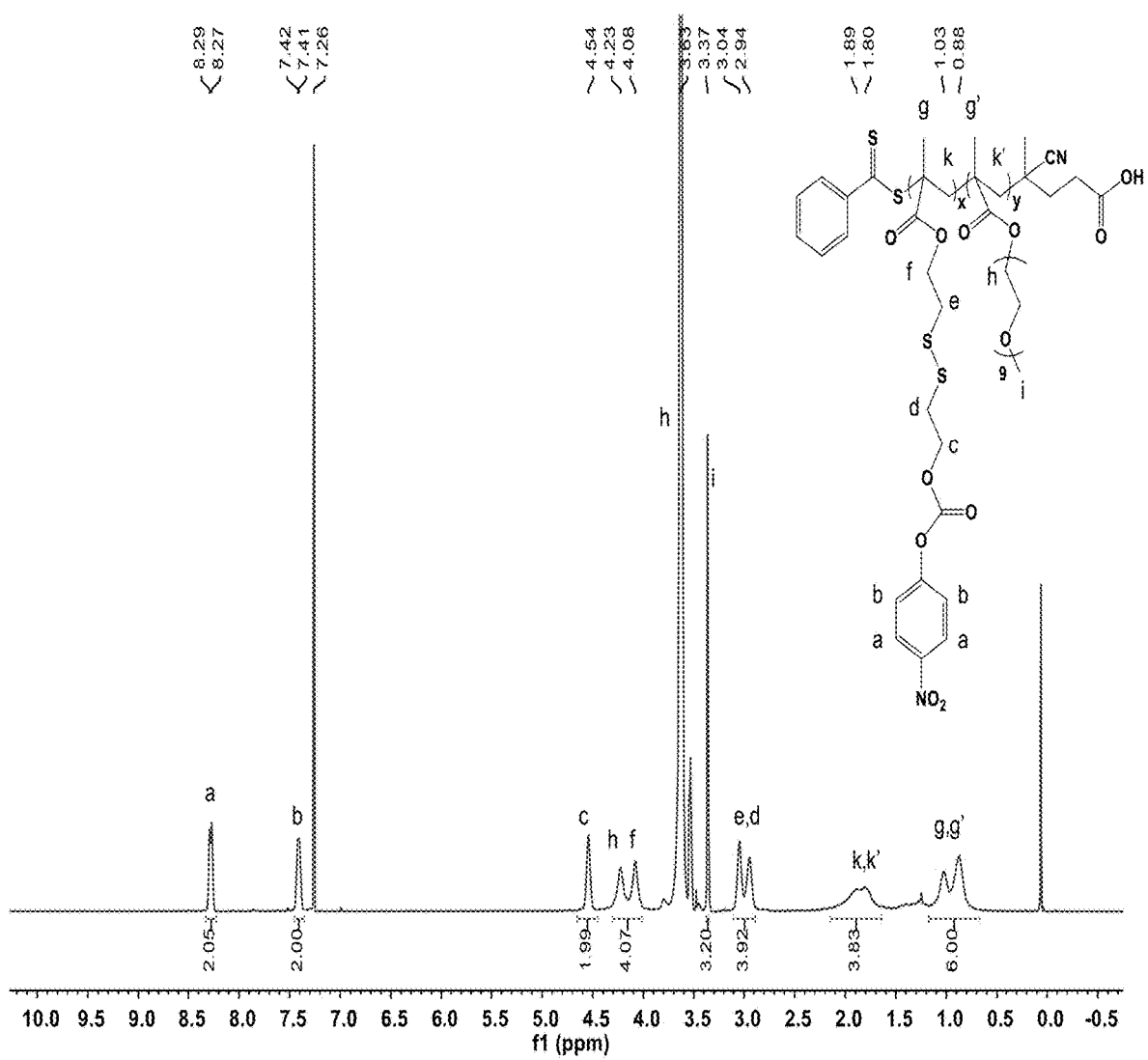
FIG. 8. $^1$H-NMR spectra of p(PEGMA-co-NPC), P1

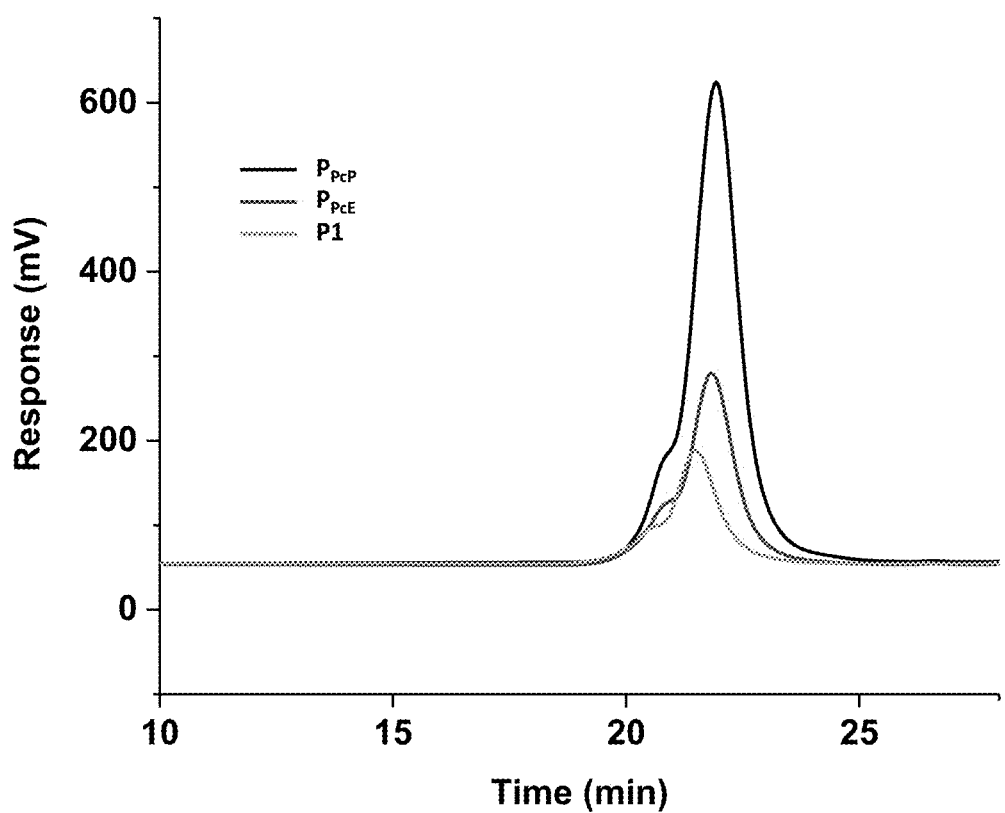
FIG. 9. GPC(THF) for polymers P$_{PcP}$, P$_{PcE}$ and P1

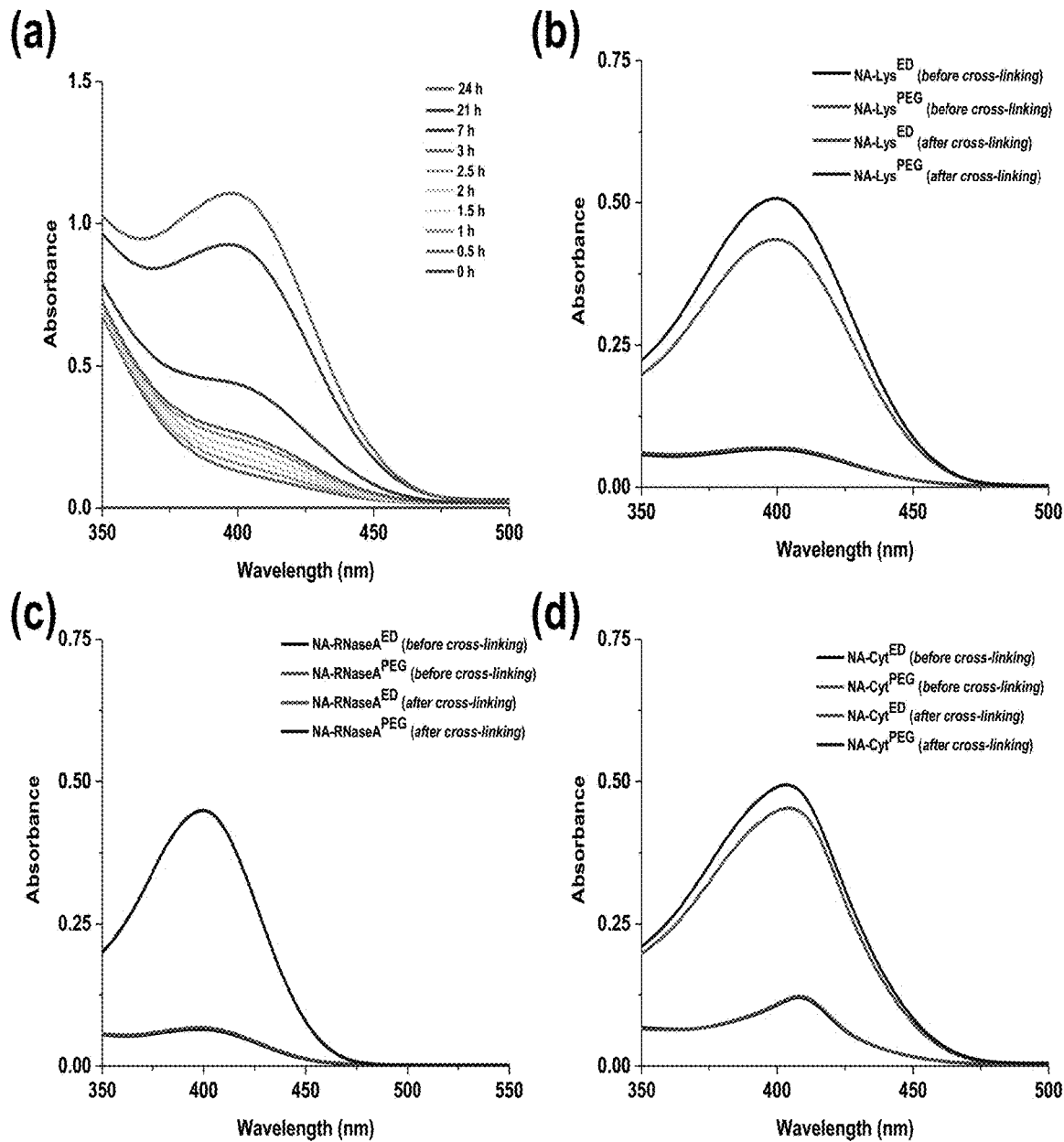
FIG. 10. (a) Time-course of absorbance profile for released 4-nitrophenol as a fate of conjugation of lysozyme with polymer P1; Absorbance spectra of polymer-protein conjugates- before and after crosslinking for (b) lysozyme; (c) RNase A and (d) cytochrome C. UV–visible absorption spectra were recorded on a PerkinElmer Lambda 35 spectrophotometer.

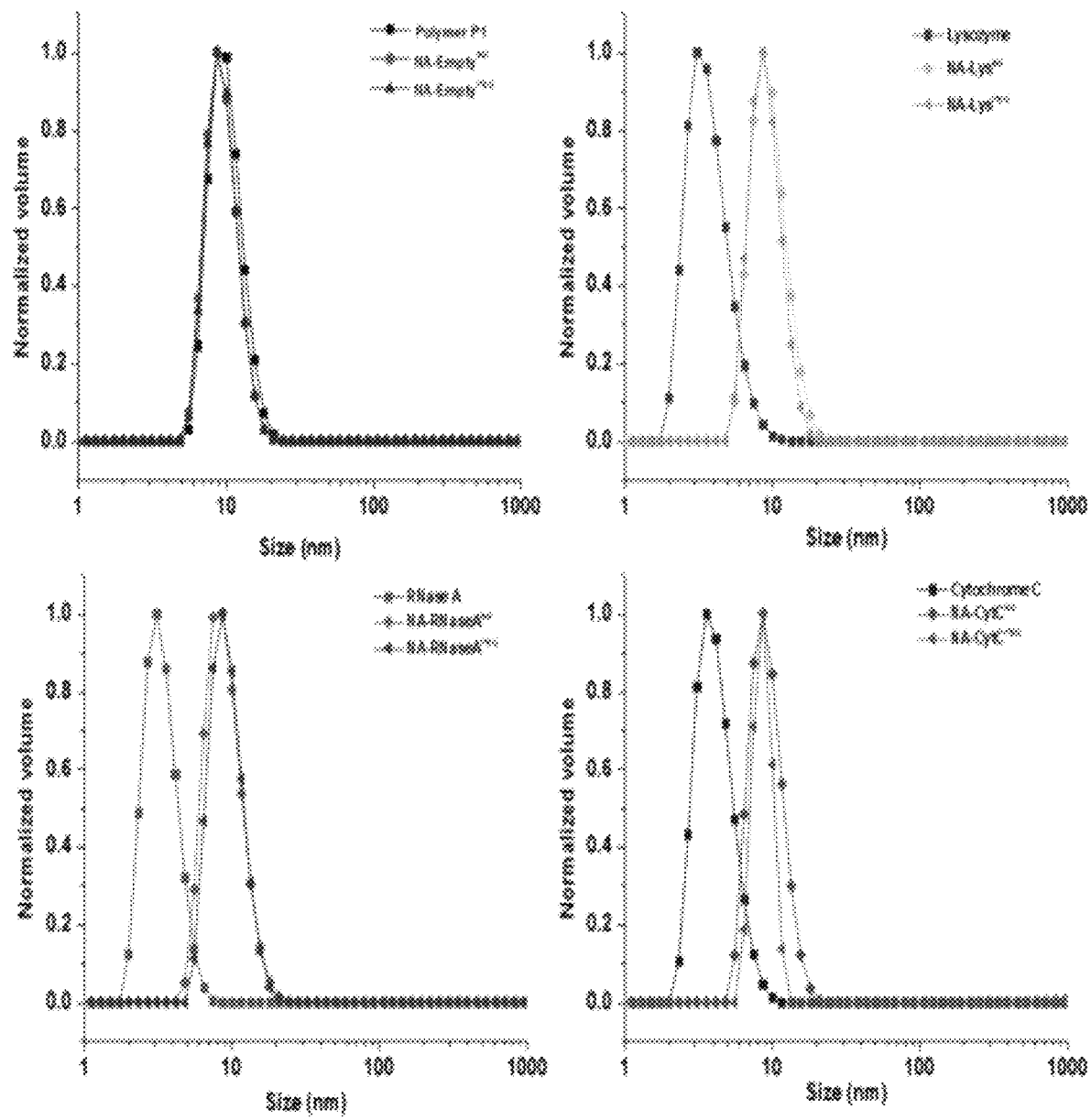
FIG. 11. Particle size analysis of protein-polymer nanoassemblies from DLS measurements

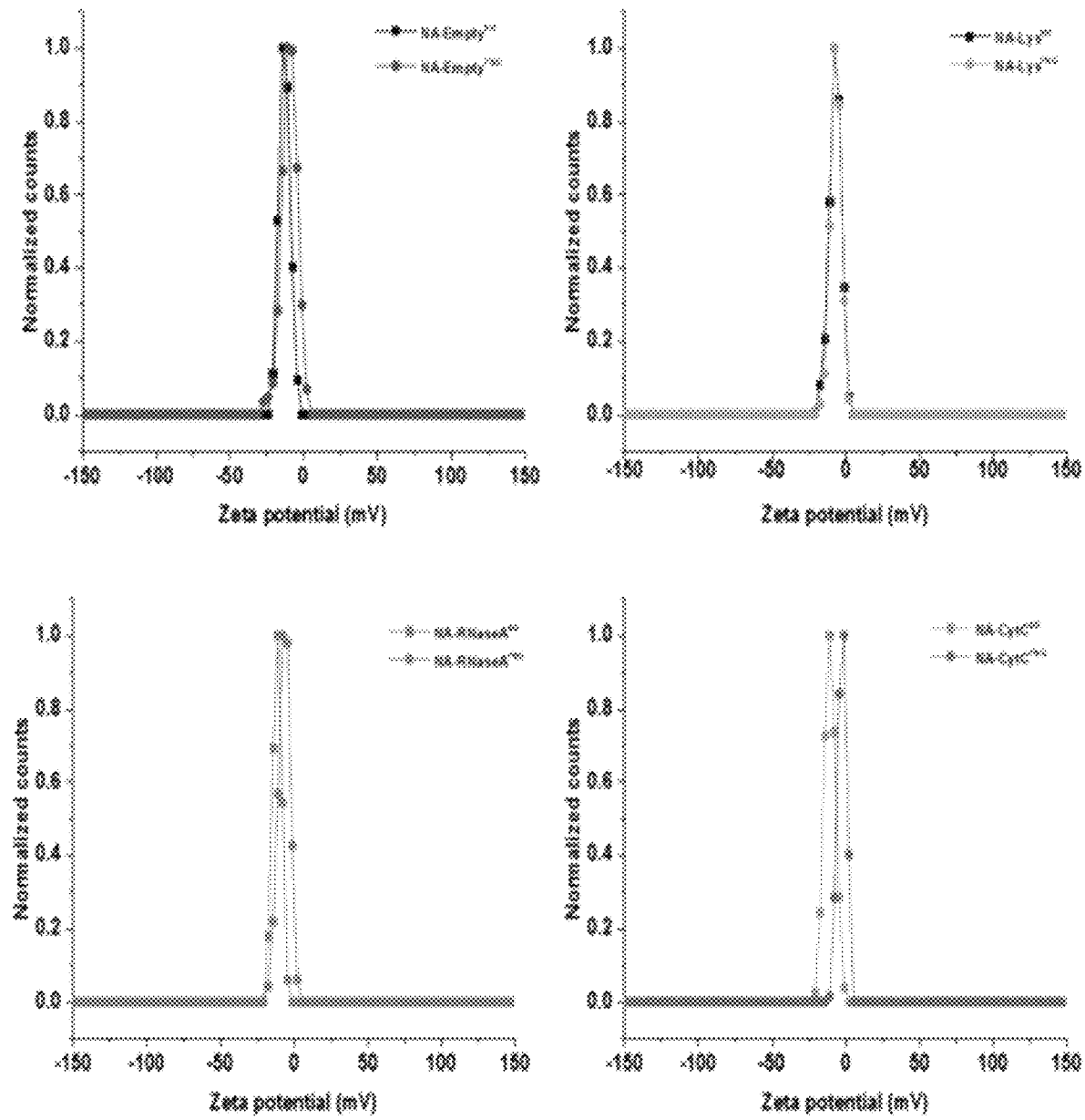
FIG. 12. Zeta potential plots for protein-polymer nanoassemblies

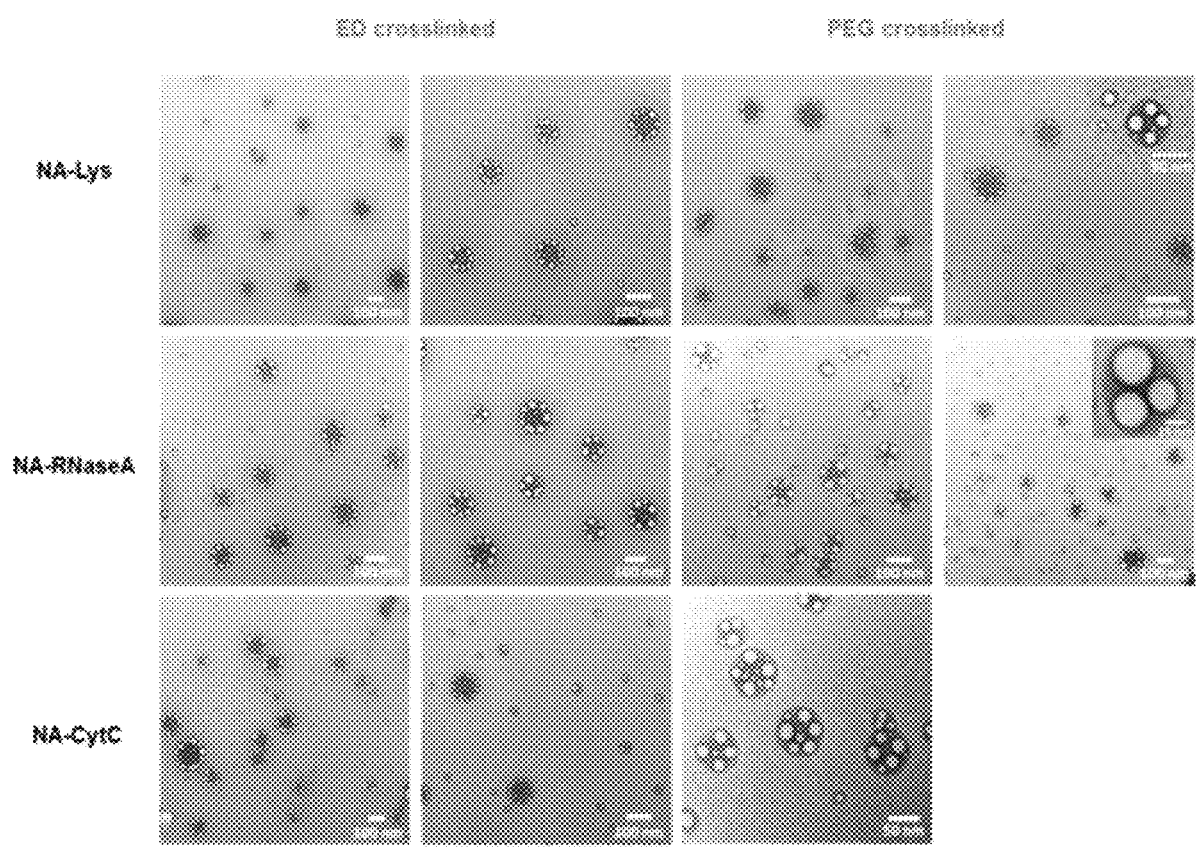
FIG. 13. TEM images for ED and PEG-crosslinked PPCs.

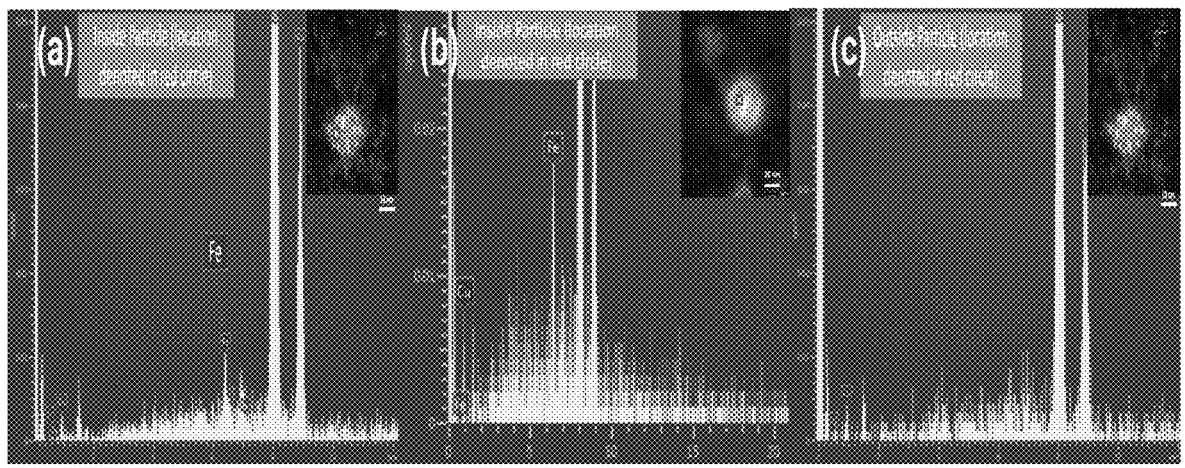
FIG. 14. EDX profile indicating Fe content inside NA-CytC$^{PEG}$ conjugates: (a, b) inside particle and (c) outside particle.
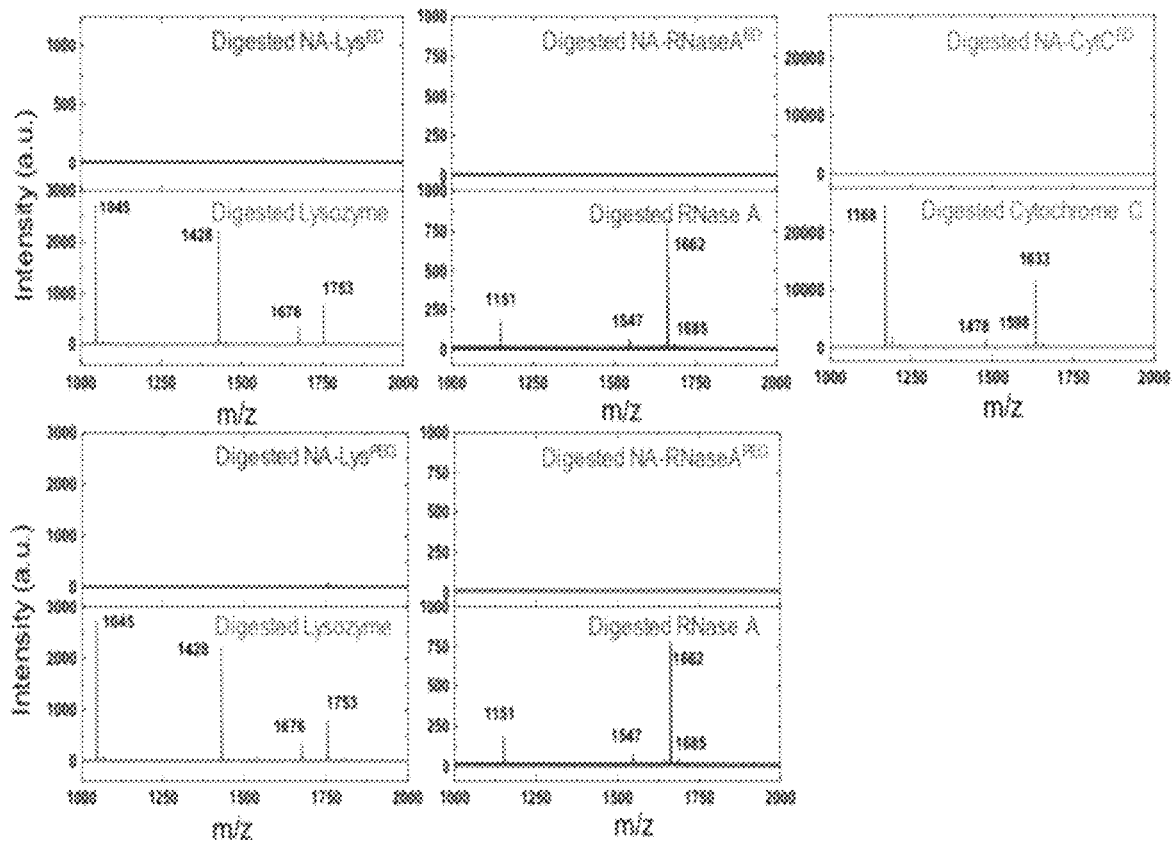
FIG. 15. Trypsin digest for ED and PEG-crosslinked polymer-protein nanoassemblies

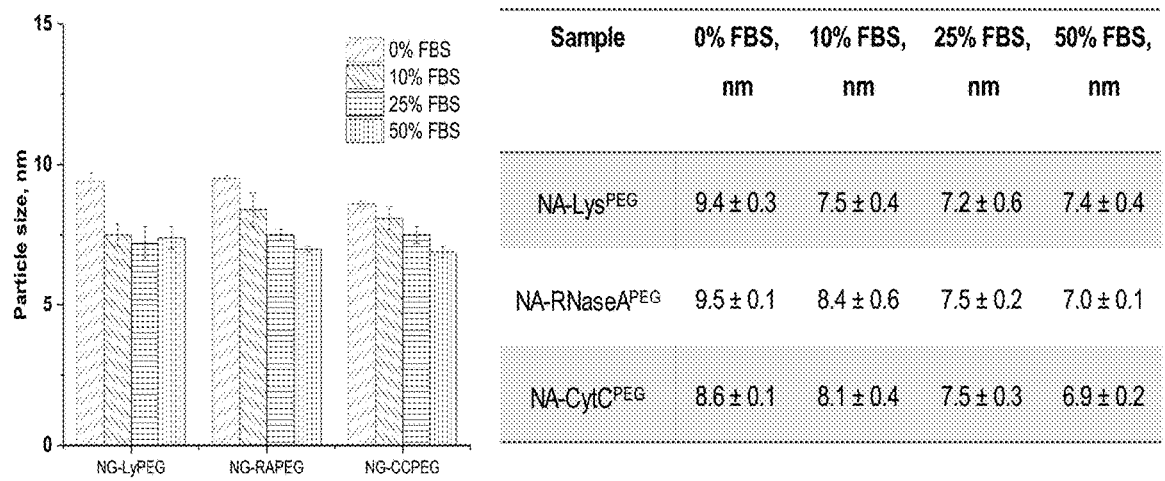
Figure 16. Particle size analysis of nanoassemblies in presence of serum
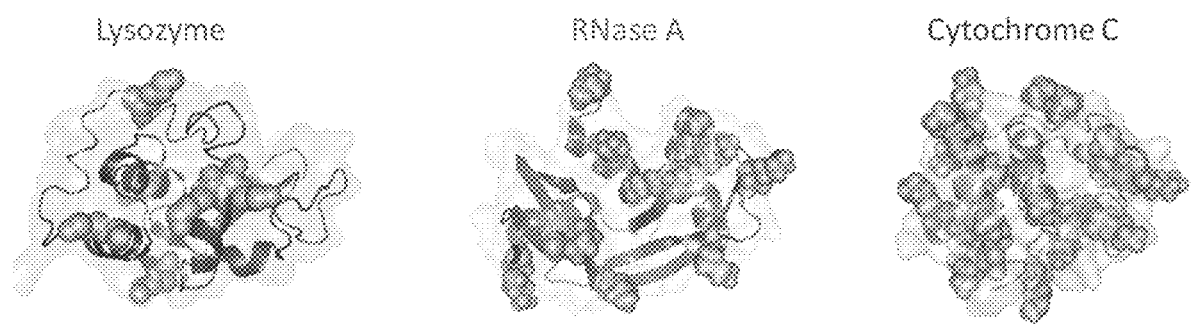
FIG. 17. Lysine residues in Lysozyme (#6), RNase A (#10) and Cytochrome C (#19)

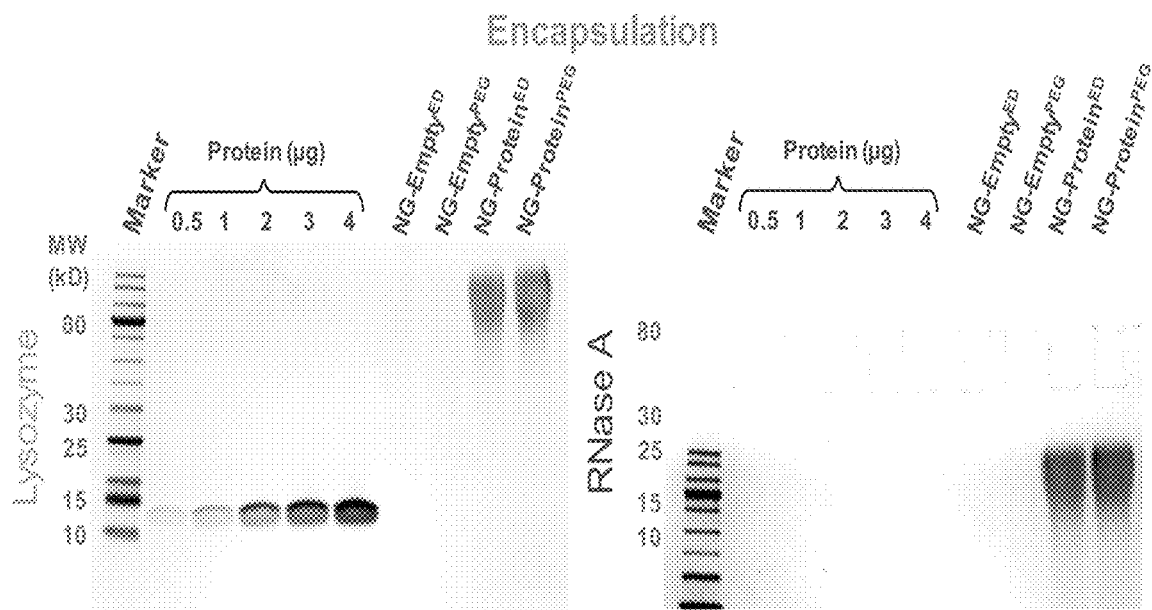
FIG. 18. SDS-PAGE for encapsulation analysis with nanoassemblies containing Lys and RNaseA
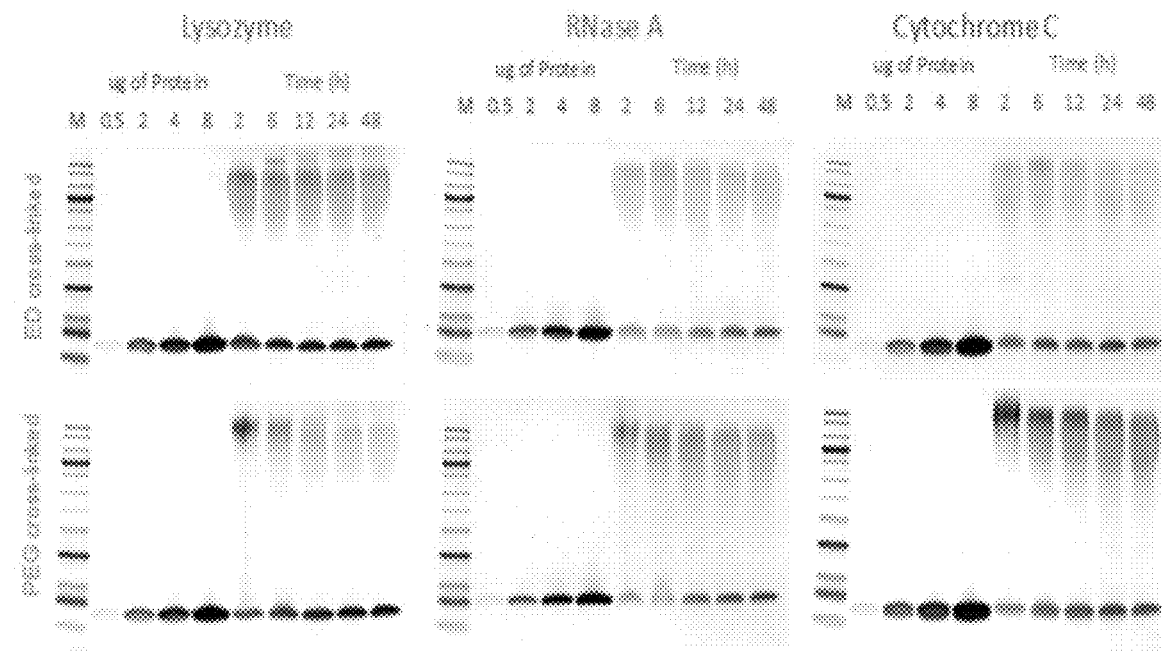
FIG. 19. Release kinetics of proteins from the nanoassemblies by SDS-PAGE at disulfide of polymer to DTT ratio 1:1

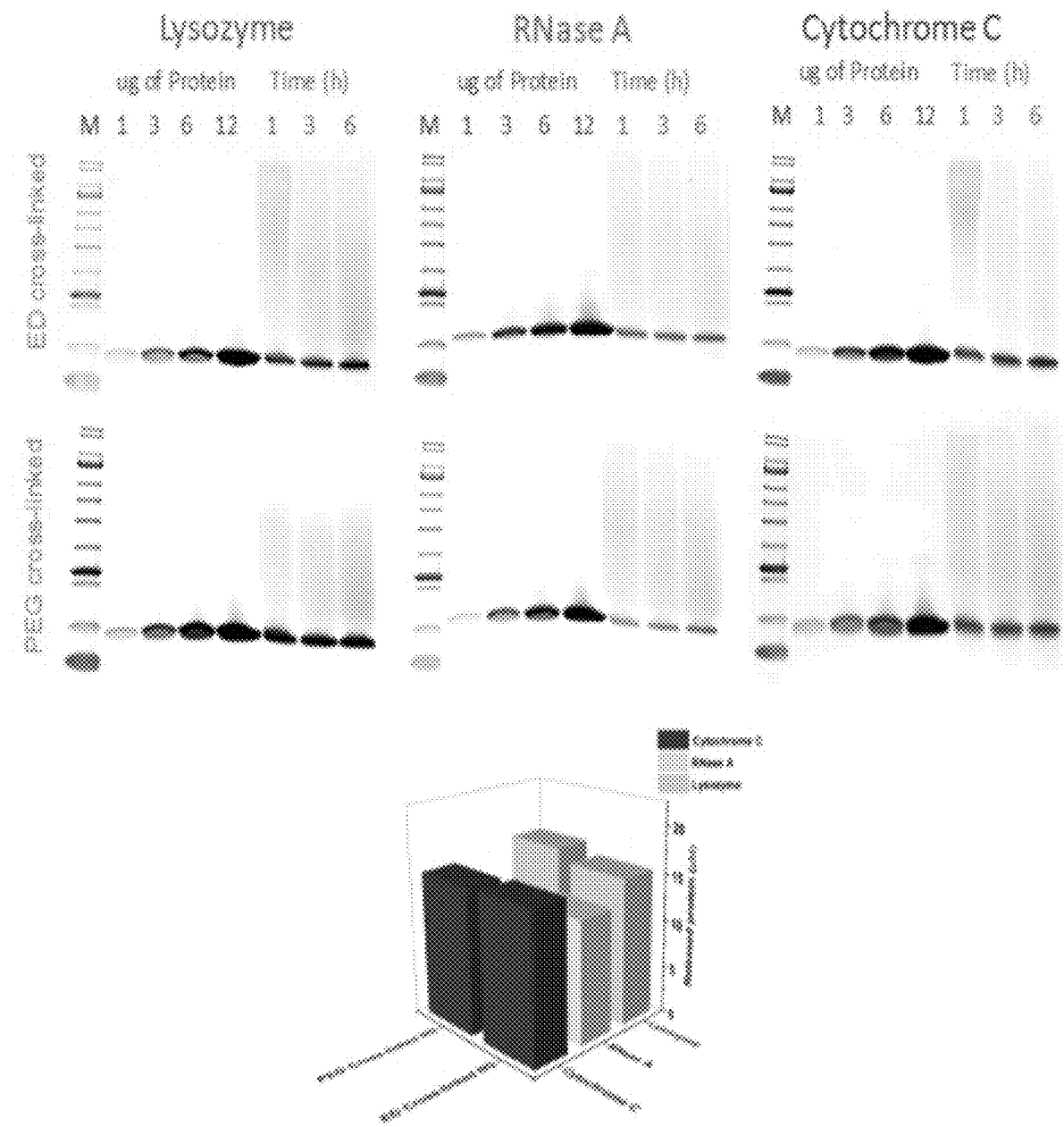
FIG. 20. Release kinetics of proteins from the PPCs by SDS-PAGE at disulfide of polymer to DTT ratio 1:10, quantification data provided in the 3D bar graph after 6 h of release.

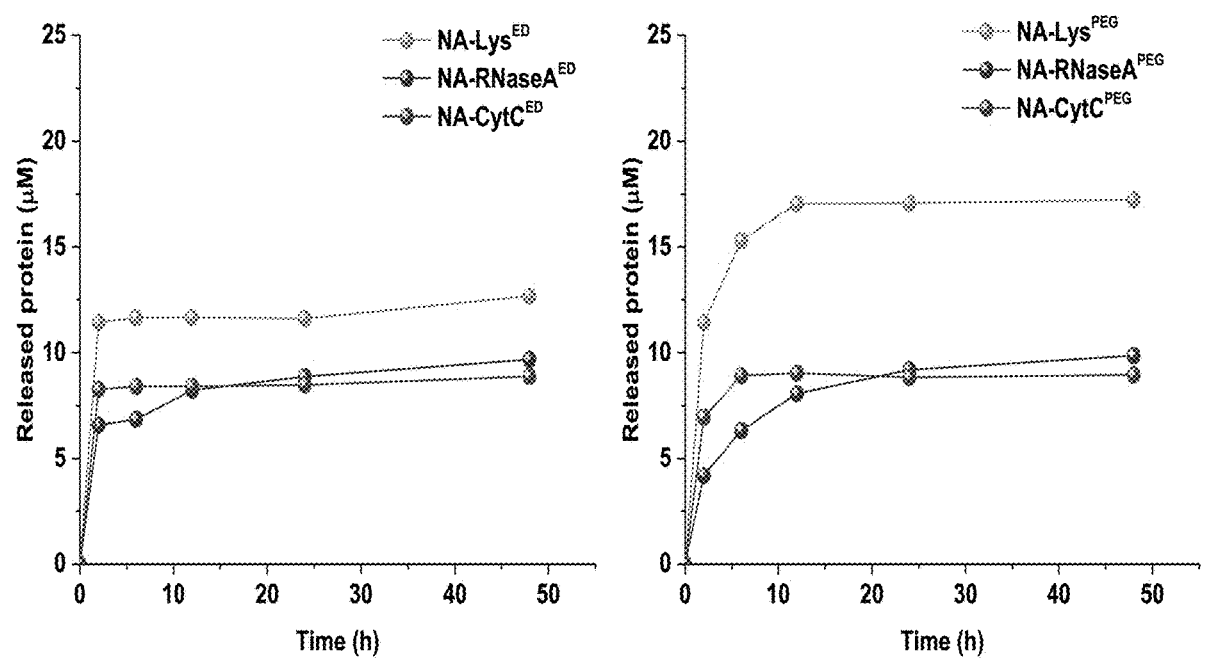
FIG. 21. Release kinetics of proteins from the nanoassemblies

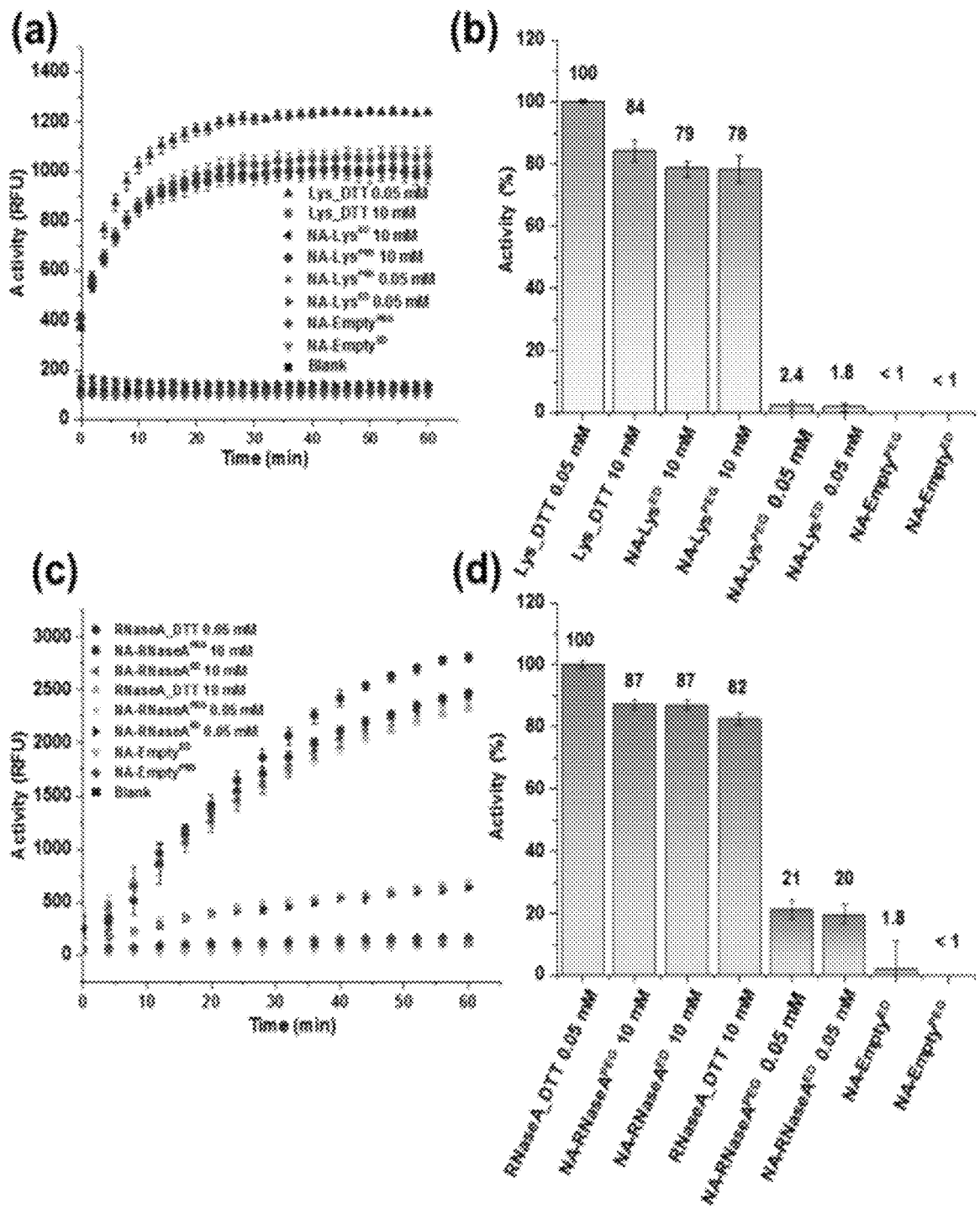
FIG. 22. Activity of released proteins from nanoassemblies containing (a-b) Lysozyme; (c-d) RNase A.

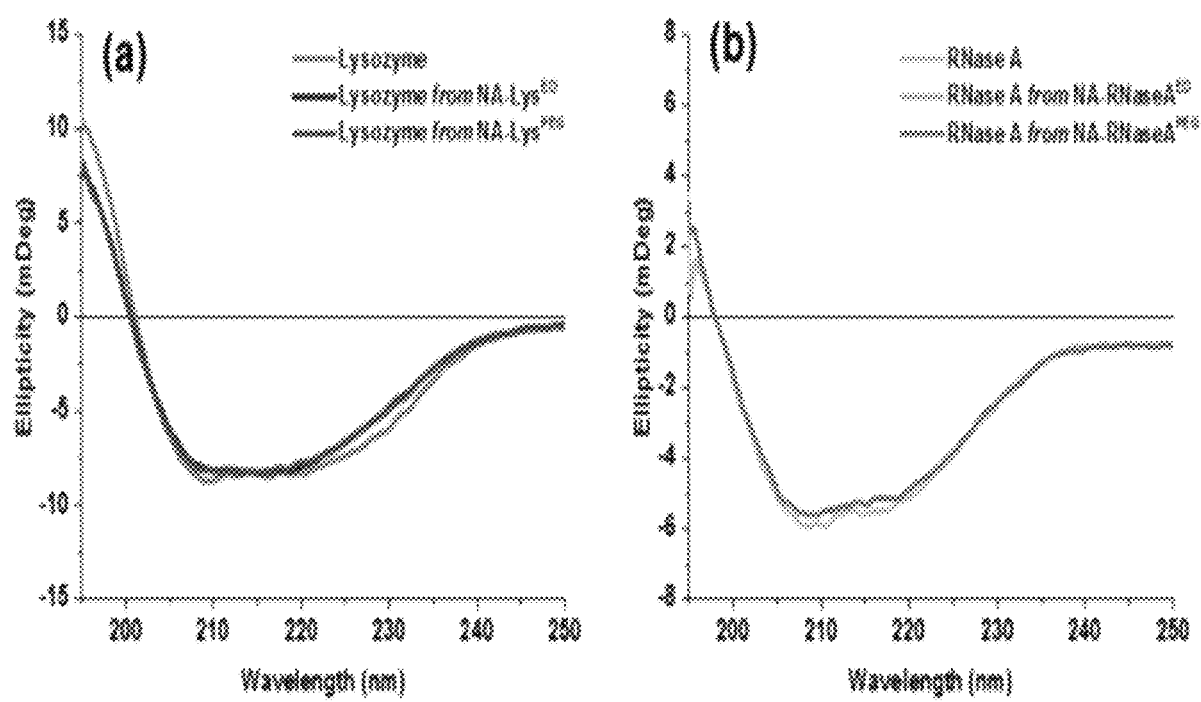
FIG. 23. CD spectra of native proteins and polymer-protein nanoassemblies

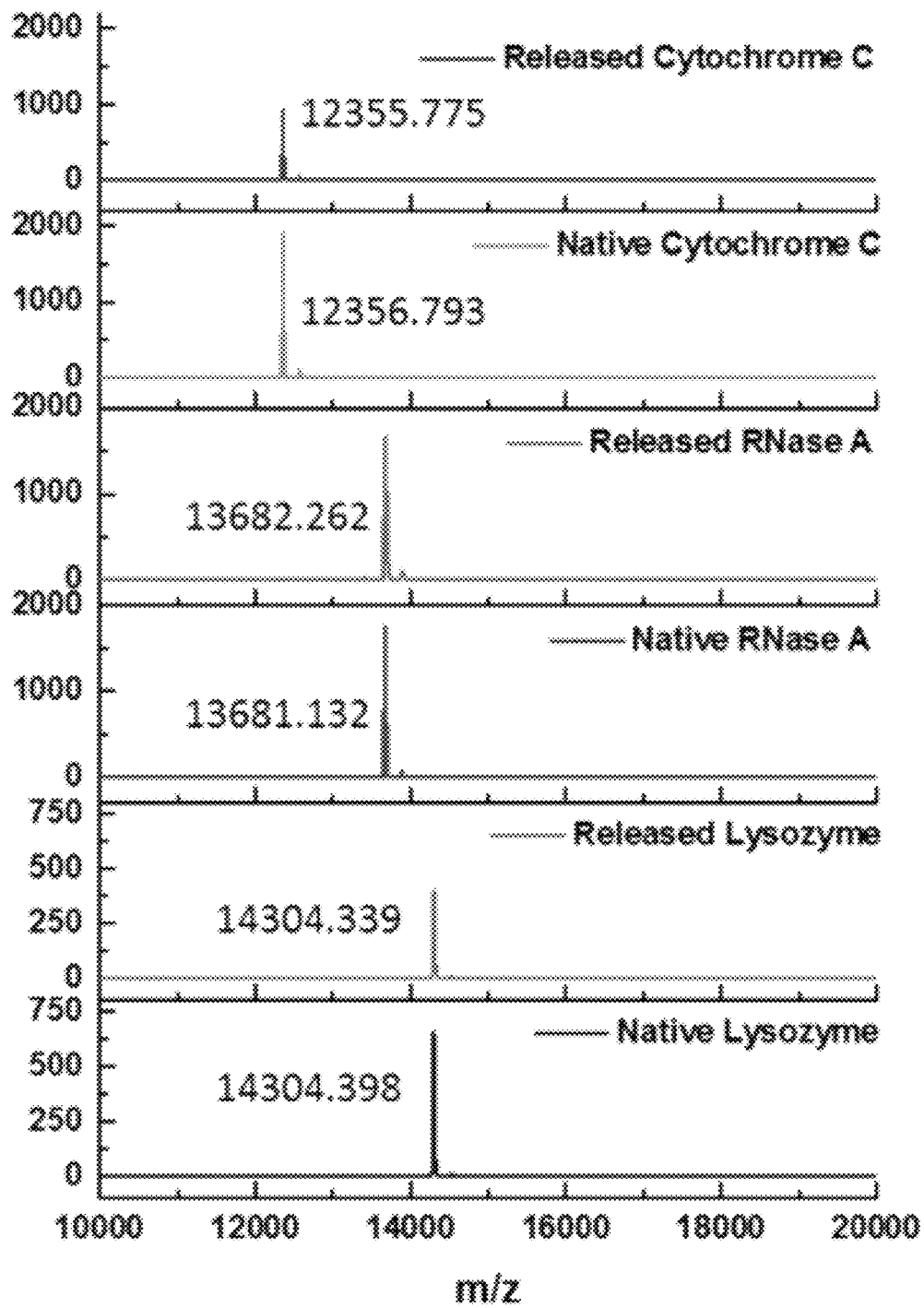
FIG. 24. Comparison of MALDI-MS spectra of the native proteins and released proteins from nanoassemblies.

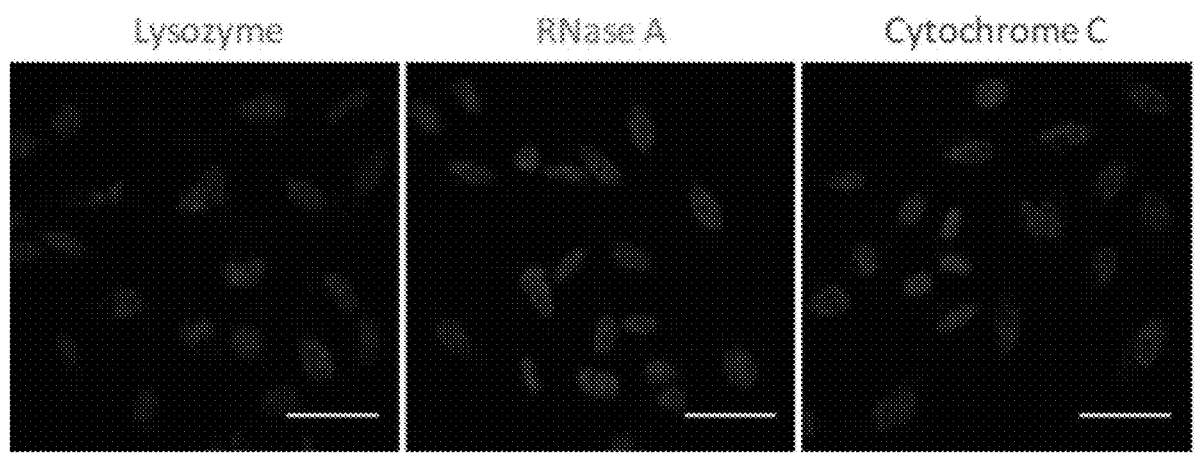
FIG. 25. Negligible uptake for HeLa cells incubated with only proteins, cell nucleus was stained with Hoechst 33342, scale bar: 50 μm.

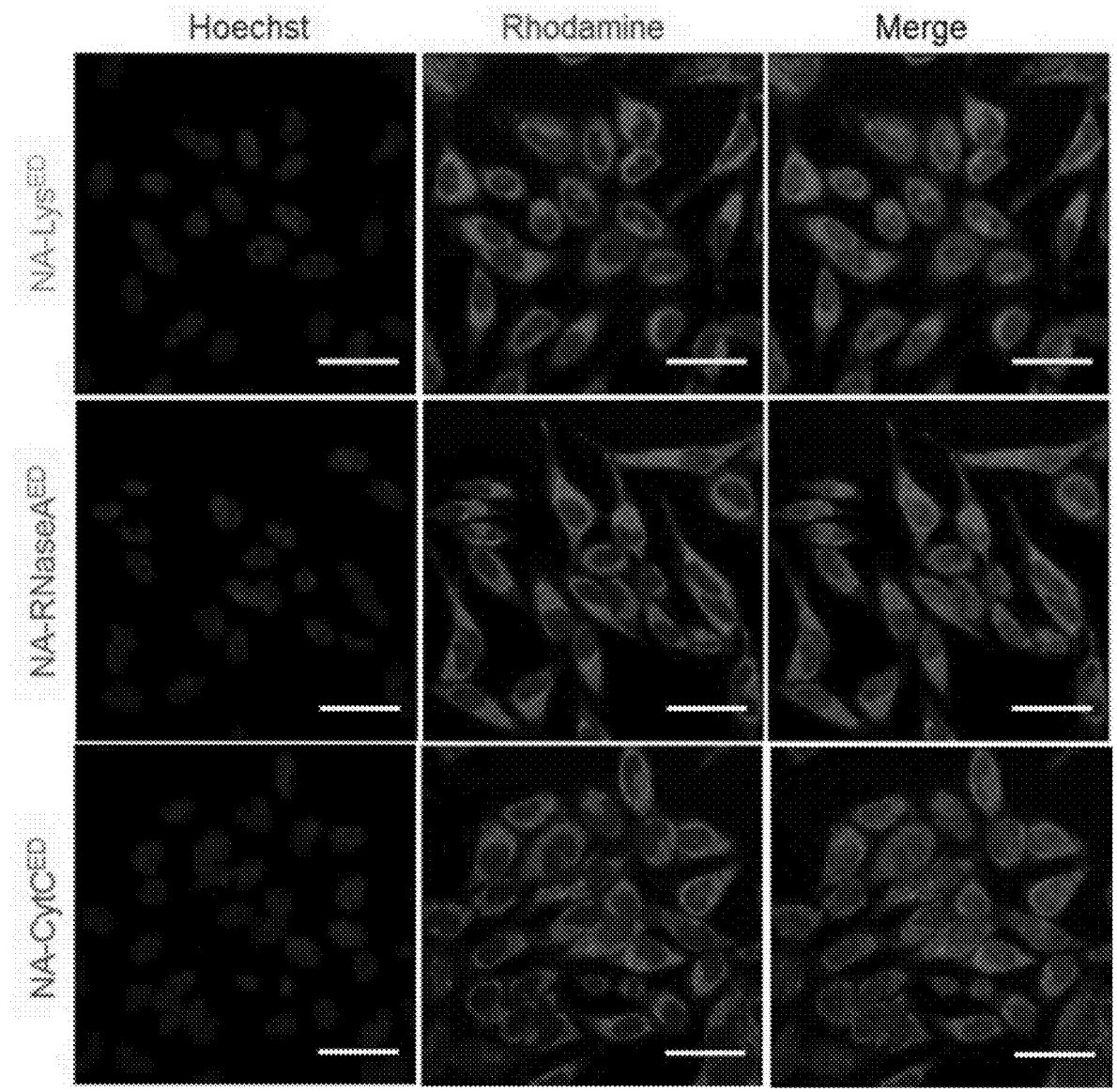
FIG. 26. Cellular internalization with ED-crosslinkied nanoassemblies, cell nucleus was stained with Hoechst 33342, scale bar: 50 μm.

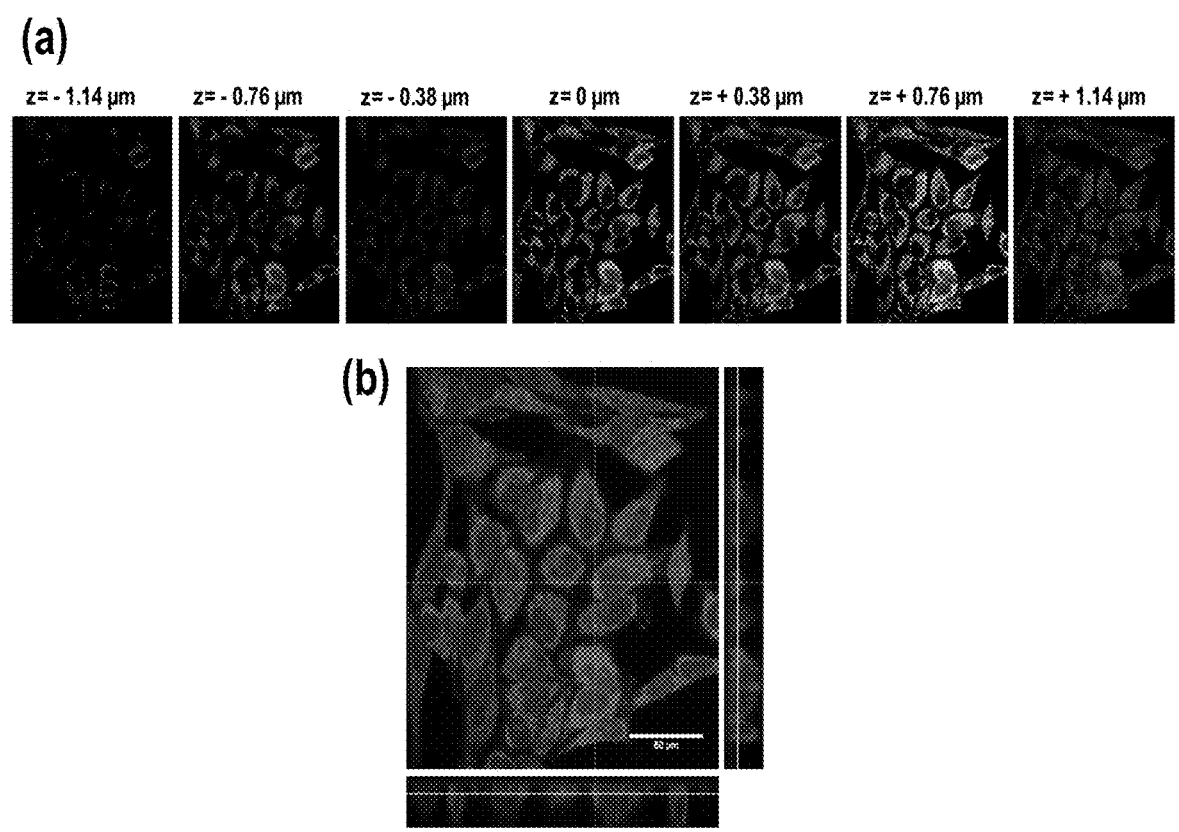
FIG. 27. (a) Depth profiling for NA-CytC$^{PEG}$ dosed nanoassemblies: pseudo-colored consecutive slices through z-axis and (b) z-stack orthogonal projection from CLSM experiment showing localization of cytochrome C inside HeLa cells.

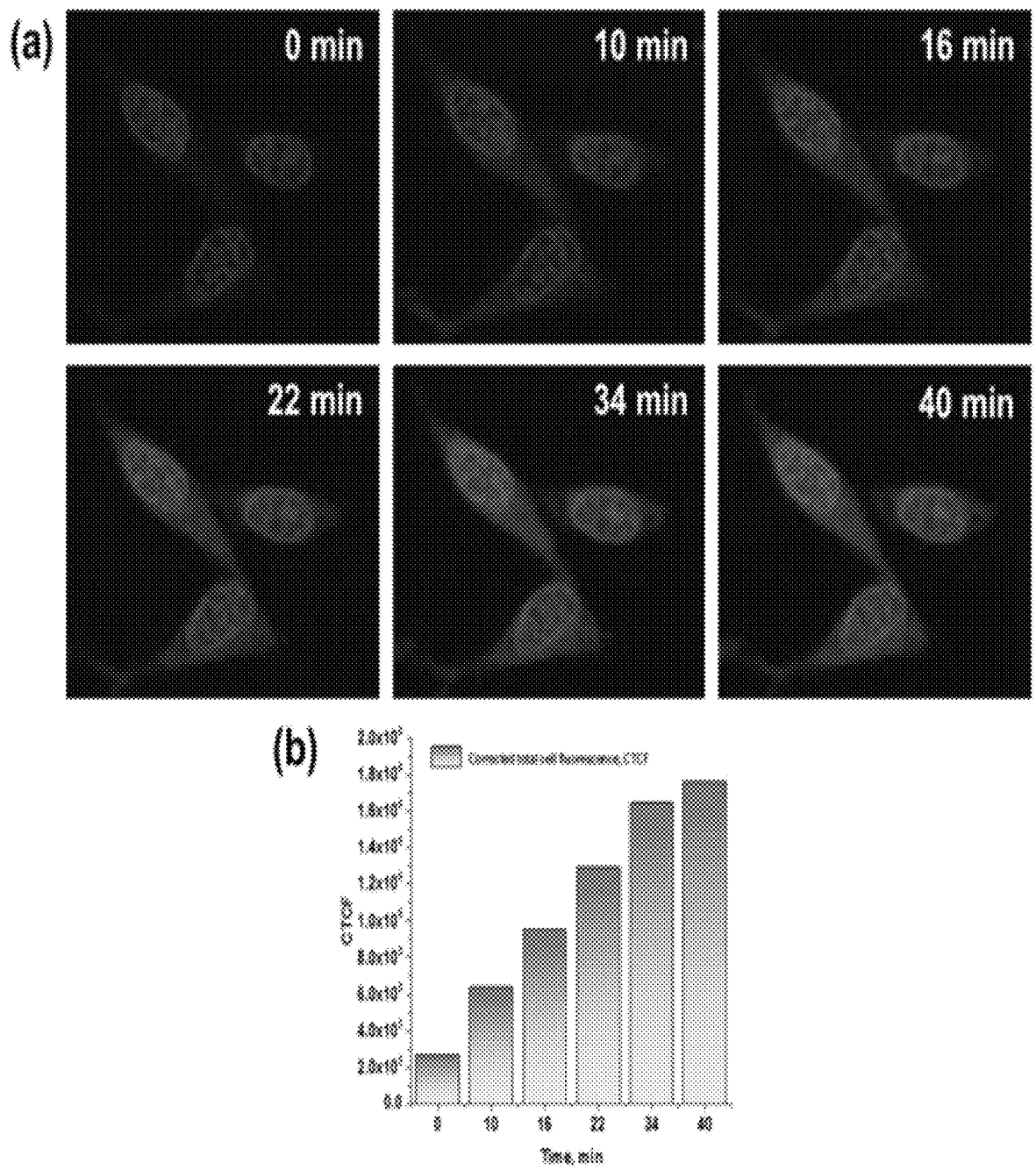
FIG. 28. (a) Time course of uptake for NA-CytC$^{PEG}$, (b) Fluorescence intensity measurement from the red channel by Image J software at different time points of uptake experiment, expressed as Corrected total cell fluorescence, CTCF = Integrated Density - (Area of selected cell × Mean fluorescence of background).

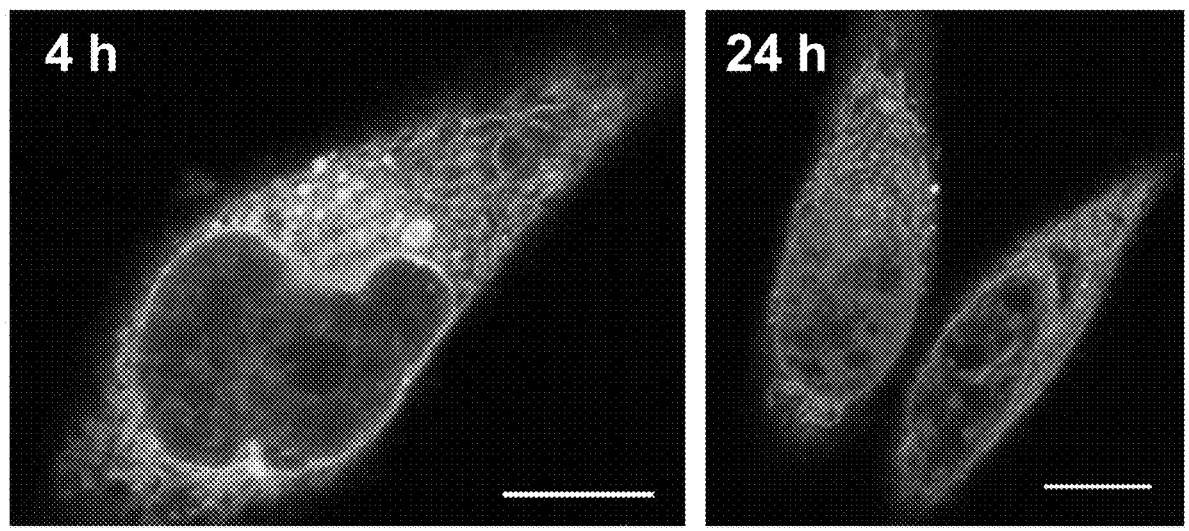
FIG. 29. Endosomal escape studies by co-localization of LysoTracker Green and Rhodamine B tagged protein; co-localization of dyes after 4 h incubation confirms existence in the endosomes and after 24 h distinct red fluorescence confirms release of proteins into the cytosol from endosomes. Scale bar: 10 μm.

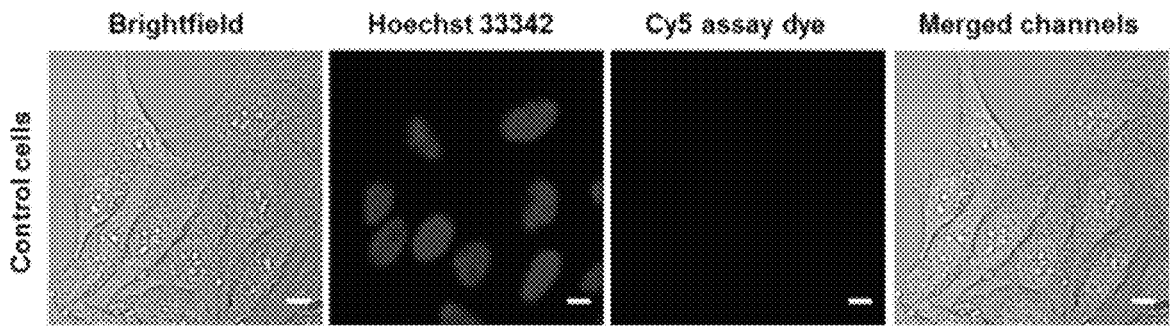

FIG. 30. Detection of activated caspase-3/7 after 72 h in control HeLa cells treated with NA-Empty[PEG] sample; scale bar: 10 μm, no co-localization of hoechst and cy5-tagged assay reagent was observed in the nucleus.

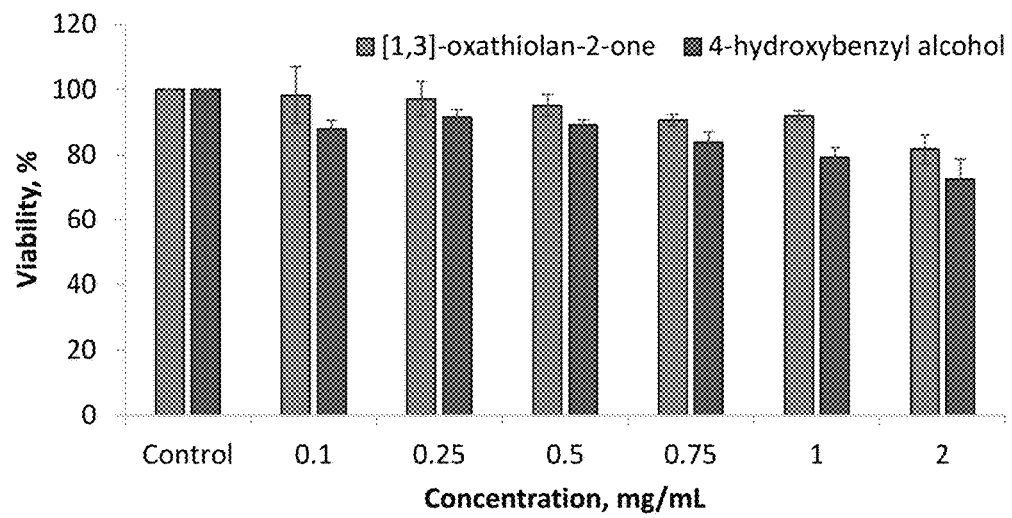

FIG. 31. Toxicity from small molecule byproducts. Upon encountering the GSH-stimulus, the polymer-protein complex will degrade to form two byproducts. These data show that both of these by products are not cytotoxic to HeLa cells.

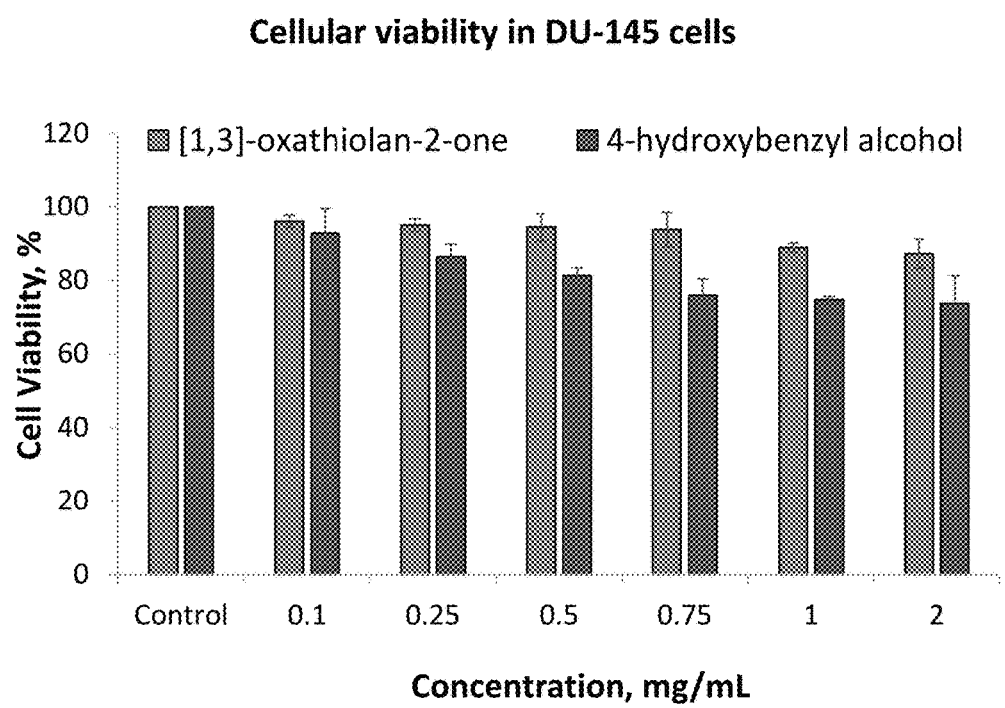
FIG. 32. Toxicity from small molecule byproducts. Upon encountering the GSH-stimulus, the polymer-protein complex will degrade to form two byproducts. These data show that both of these by products are not cytotoxic to DU-145 cells.

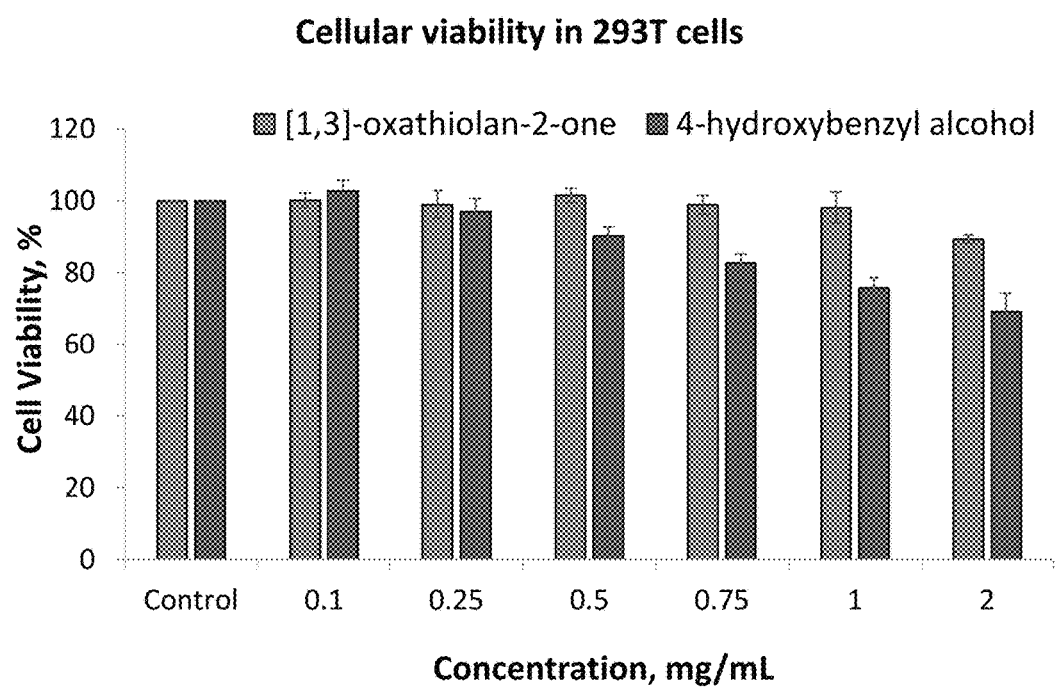
FIG. 33. Toxicity from small molecule byproducts. Upon encountering the GSH-stimulus, the polymer-protein complex will degrade to form two byproducts. These data show that both of these by products are not cytotoxic to 293T cells.

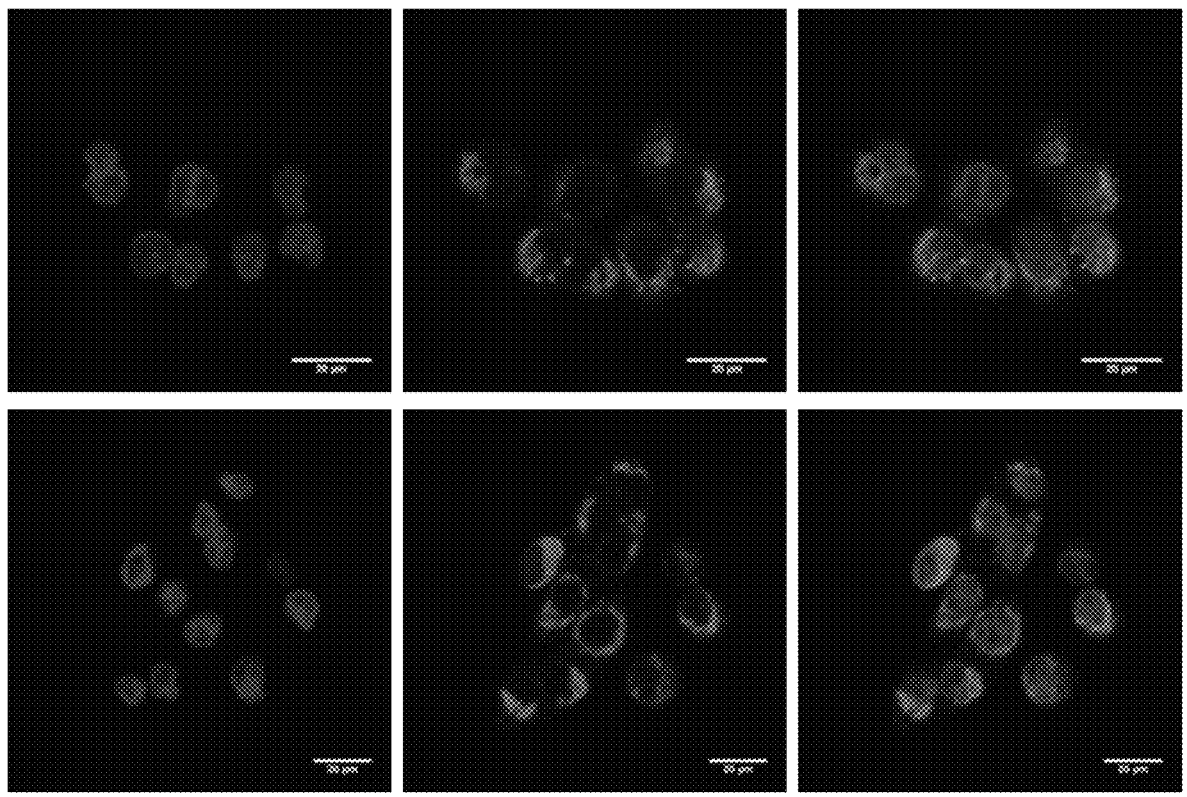
FIG. 34. Cellular uptake of NA-CC-PEG (Rhodamine tagged Cytochrome C) in DU-145 cell lines.

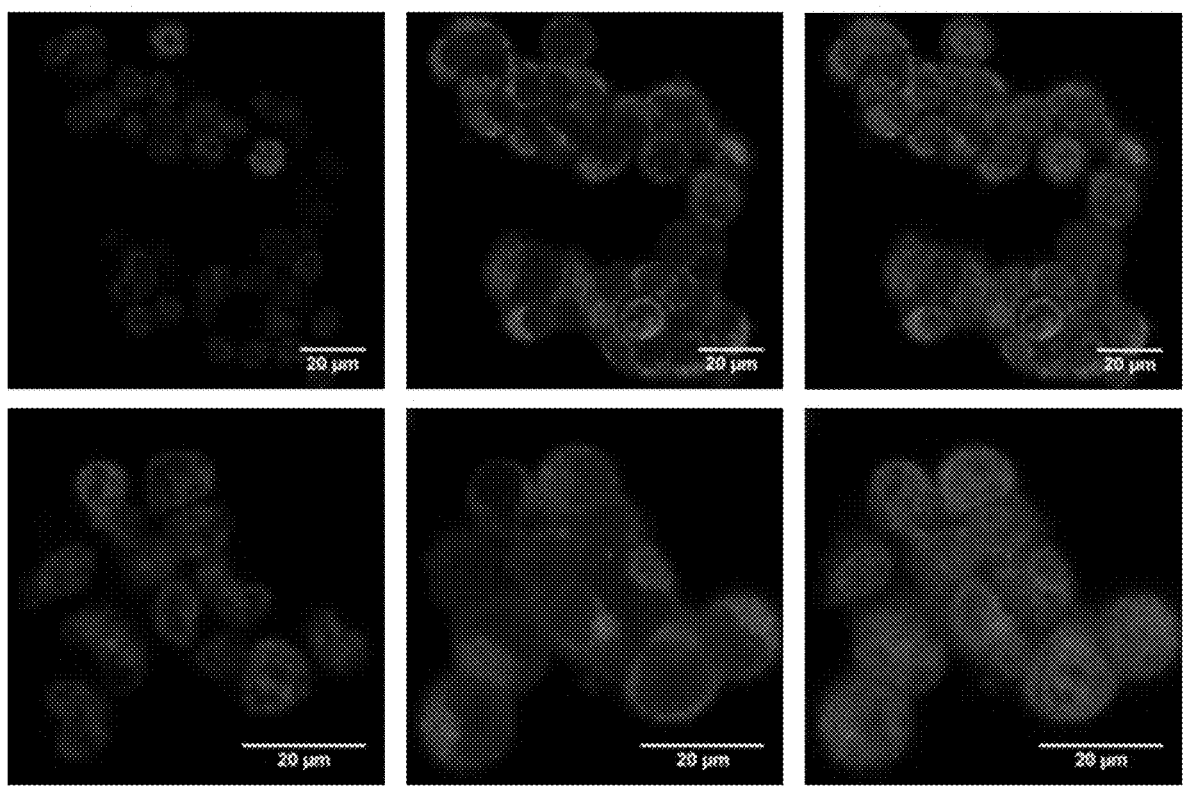
FIG. 35. Cellular uptake of NA-CC-PEG (Rhodamine tagged Cytochrome C) in 293T cell lines.

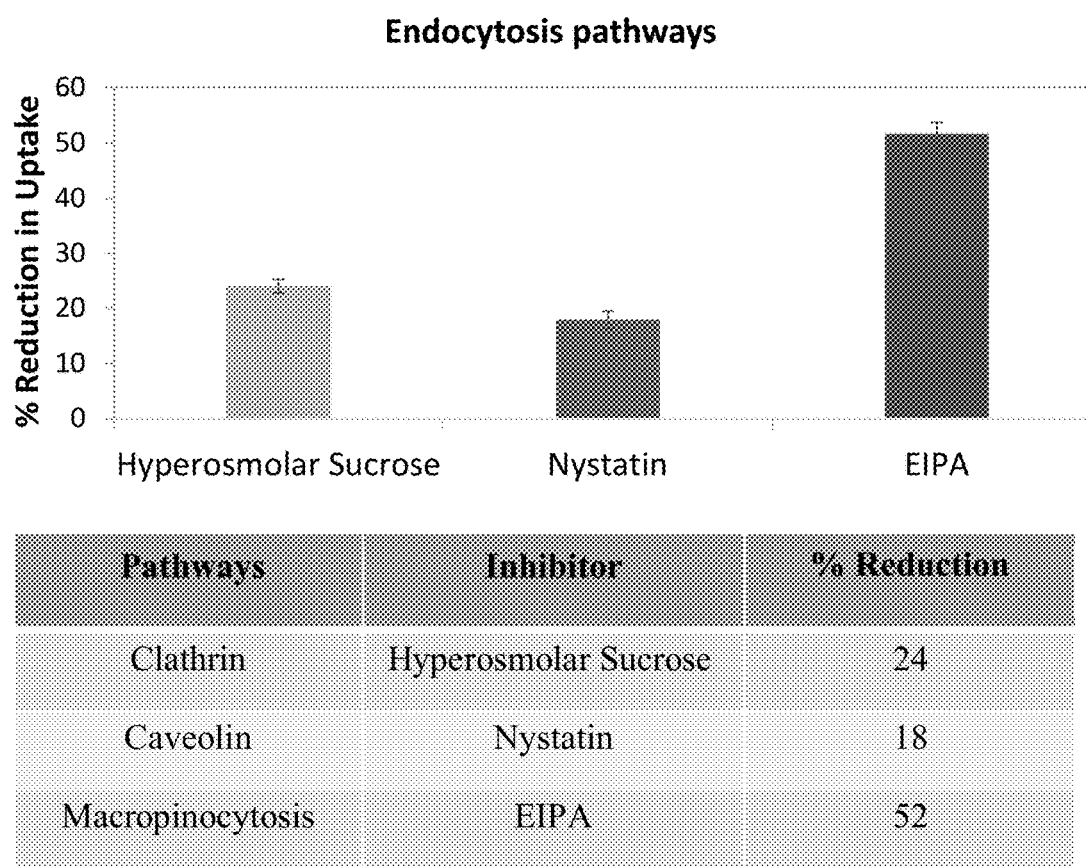
FIG. 36. Evaluation of uptake pathways using pathway inhibtiors. The major forms of uptake for the Cytochrome C-incorporated polymer nanoassembly are macropinocytosis and clathrin mediated endocytosis.

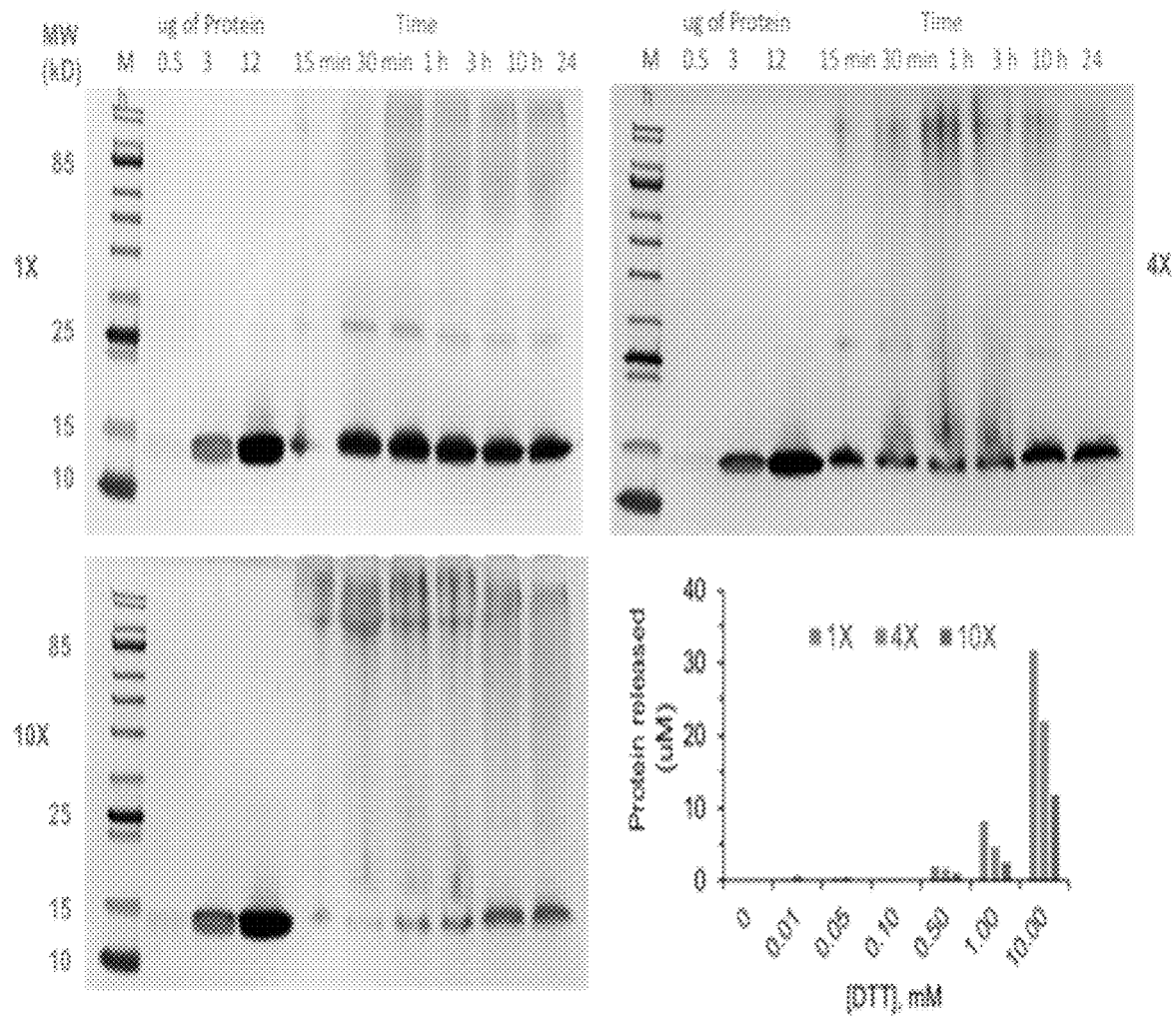
FIG. 37. Crosslinking with 1, 4 and 10 eqv. of diamine (secondary crosslinker) was examined to test the control over protein release. With increasing secondary crosslink density, the release kinetics became slower reflected by the time dependent release studies.

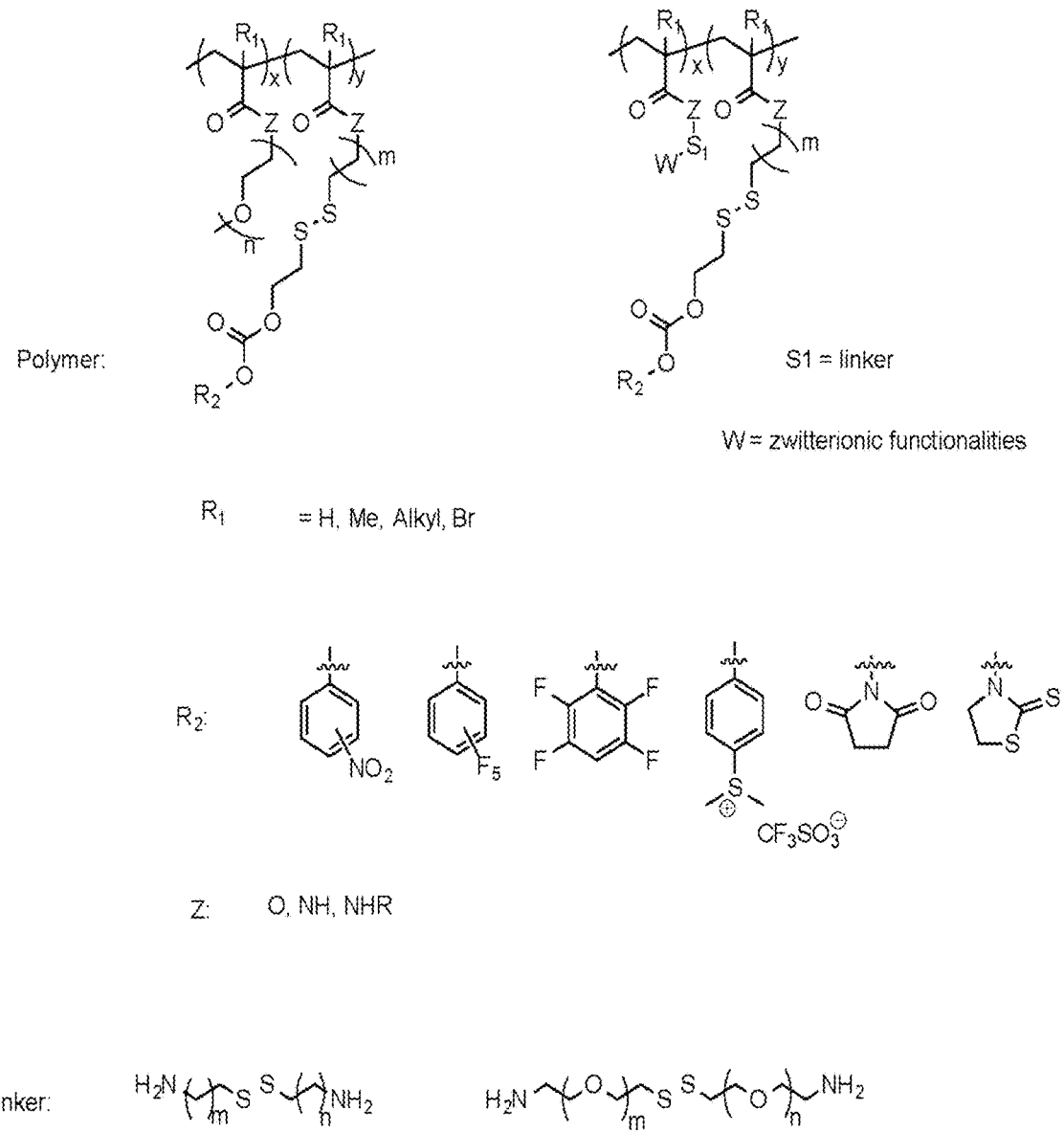
FIG. 38. Exemplary polymer crosslinking using disulfide a crosslinker.

SEQUENCE LISTING

<160> NUMBER OF SEQ ID NOS: 13

<210> SEQ ID NO 1
<211> LENGTH: 9
<212> TYPE: PRT
<213> ORGANISM: Homo sapiens

<400> SEQUENCE: 1

Gly Thr Asp Val Gln Ala Trp Ile Arg
1               5

<210> SEQ ID NO 2
<211> LENGTH: 12
<212> TYPE: PRT
<213> ORGANISM: Homo sapiens

<400> SEQUENCE: 2

Phe Glu Ser Asn Phe Asn Thr Gln Ala Thr Asn Arg
1               5                   10

<210> SEQ ID NO 3
<211> LENGTH: 15
<212> TYPE: PRT
<213> ORGANISM: Homo sapiens

<400> SEQUENCE: 3

Ile Val Ser Asp Gly Asn Gly Met Asn Ala Trp Val Ala Trp Arg
1               5                   10                  15

<210> SEQ ID NO 4
<211> LENGTH: 16
<212> TYPE: PRT
<213> ORGANISM: Homo sapiens

<400> SEQUENCE: 4

Asn Thr Asp Gly Ser Thr Asp Tyr Gly Ile Leu Gln Ile Asn Ser Arg
1               5                   10                  15

<210> SEQ ID NO 5
<211> LENGTH: 10
<212> TYPE: PRT
<213> ORGANISM: Homo sapiens

<400> SEQUENCE: 5

Met Pro Ala Pro Ala Thr Thr Tyr Glu Arg
1               5                   10

<210> SEQ ID NO 6
<211> LENGTH: 14
<212> TYPE: PRT
<213> ORGANISM: Homo sapiens

<400> SEQUENCE: 6

Leu Trp Ser Ser Leu Thr Leu Leu Gly Ser Tyr Lys Gly Lys
1               5                   10

<210> SEQ ID NO 7
<211> LENGTH: 14
<212> TYPE: PRT
<213> ORGANISM: Homo sapiens

<400> SEQUENCE: 7

Met Pro Ala Pro Ala Thr Thr Tyr Glu Arg Ile Val Tyr Lys
1               5                   10

<210> SEQ ID NO 8
<211> LENGTH: 16
<212> TYPE: PRT
<213> ORGANISM: Homo sapiens

<400> SEQUENCE: 8

Leu Glu Phe Gln Asp Gly Gly Val Gly Leu Thr Ala Ala Gln Phe Lys
1               5                   10                  15

<210> SEQ ID NO 9
<211> LENGTH: 11
<212> TYPE: PRT
<213> ORGANISM: Homo sapiens

<400> SEQUENCE: 9

Thr Gly Pro Asn Leu His Gly Leu Phe Gly Arg
1               5                   10

<210> SEQ ID NO 10
<211> LENGTH: 12
<212> TYPE: PRT
<213> ORGANISM: Homo sapiens

<400> SEQUENCE: 10

Lys Thr Glu Arg Glu Asp Leu Ile Ala Tyr Leu Lys
1               5                   10

<210> SEQ ID NO 11
<211> LENGTH: 12
<212> TYPE: PRT
<213> ORGANISM: Homo sapiens

<400> SEQUENCE: 11

Thr Glu Arg Glu Asp Leu Ile Ala Tyr Leu Lys Lys
1               5                   10

<210> SEQ ID NO 12
<211> LENGTH: 15
<212> TYPE: PRT
<213> ORGANISM: Homo sapiens

<400> SEQUENCE: 12

Lys Thr Gly Gln Ala Pro Gly Phe Thr Tyr Thr Asp Ala Asn Lys
1               5                   10                  15

<210> SEQ ID NO 13
<211> LENGTH: 14
<212> TYPE: PRT
<213> ORGANISM: Homo sapiens

<400> SEQUENCE: 13

Ile Phe Val Gln Lys Cys Ala Gln Cys His Thr Val Glu Lys
1               5                   10

PROTEIN-TEMPLATED SELF-ASSEMBLY OF A COVALENT POLYMER NETWORK FOR INTRACELLULAR TRAFFICKING AND TRACELESS RELEASE

PRIORITY CLAIMS AND RELATED PATENT APPLICATIONS

This application is the U.S. national phase of and claims priority to PCT/US18/25580, filed Mar. 30, 2018, which claims the benefit of priority to U.S. Provisional Application Ser. No. 62/478,820, filed on Mar. 30, 2017, the entire content of which is incorporated herein by reference.

STATEMENT REGARDING FEDERALLY FUNDED RESEARCH OR DEVELOPMENT

This invention was made with government support under W911NF-15-1-0568 from the Army Research Office. The government has certain rights in the invention.

TECHNICAL FIELDS OF THE INVENTION

The invention generally relates to polymers and polymer-based nano-structures. More particularly, the invention relates to polymers and polymer network which biomolecules (e.g., proteins, antibodies, peptide aptamers) can be covalently conjugated to and stably encapsulated in and be controllably delivered and released upon degradation of the nano-structures in response to specific microenvironment, and compositions and methods of preparation and use thereof.

BACKGROUND OF THE INVENTION

Protein therapeutics have gained much attention recently as they directly address genetic deficiencies and therefore mitigates side-effects that have plagued many small molecule drugs. (Leader, et al. 2008 *Nat. Rev. Drug Discovery* 7, 21.) Potential side-effects from small molecule binders are understandable, as these molecules must be designed to target a specific protein in the complex human biological system, highlighted by the nearly 20,000 protein-encoding genes that are believed to be part of the human genome. On the other hand, proteins can directly compensate for a specific deficiency and therefore the drug development is less heuristic.

The in vivo instability and immunogenicity of macromolecular drugs, however, has hindered the development of protein-based therapeutics. Various approaches to modify protein surfaces have been taken with limited success, for example, PEGylation to enhance protein circulation lifetimes. More recently, strategies that allow for attaching other polymers to proteins have been developed in order to endow these conjugates with stimulus-responsive characteristics or to realize new self-assembled structures. (Cobo, et al. 2014 *Nat. Mater.* 14, 143; Gu, et al. 2011 *Chem. Soc. Rev.* 40, 3638-3655; Abuchowski, et al. 1977 *J. Biol. Chem.* 252, 3578; Stayton, et al. 1995 *Nature* 378, 472; Lu, et al. 2014 *Controlled Rel.* 194, 1; Hannink, et al. 2001 *Angew. Chem., Int. Ed.* 40, 4732; Moatsou, et al. 2015 *Bioconjugate Chem.* 26, 1890 and references therein; Alconcel, et al. 2011 *Polym. Chem.* 2, 1442.)

Trafficking proteins and other biological macromolecules across a cellular membrane remains a critical component in the realization of effective protein and other biological therapeutics. A robust and sustainable delivery strategy demands not only a good protection of the cargo, but also for reversibility in conjugation and activity.

Two limiting approaches have been taken to address this need, both of which involve non-covalent self-assembly. First involves electrostatic binding of proteins to complementarily charged polymers and nanoparticles. (Ray, et al. 2015 *Bioconjugate Chem.* 26, 1004; Lee, et al. 2009 *Angew. Chem. Int. Ed.* 48, 5309; González-Toro, et al. 2012 *J. Am. Chem. Soc.* 134, 6964.) The second approach includes encapsulating proteins in water-filled compartments, such as liposomes. (Swaminathan, et al. 2012 *Expert Opin. Drug Deliv.* 9, 1489.) A significant limitation of the former approach is the non-specific fouling of the complex' surfaces due to electrostatic interactions and the associated toxicities. (Lv, et al. 2006 *J. Controlled Release* 114, 100.) The latter approach has the potential to address the fouling issues, but is fraught with low loading capacities, especially when charge-neutral lipids are used.

Accordingly, major hurdles remain in the pursuit of effective delivery of biomolecules inside cells. Novel strategies, along with novel delivery vehicles and release methodologies are keenly desired.

SUMMARY OF THE INVENTION

The invention provides polymers and polymer network to which biomolecules (e.g., proteins, enzymes, antibodies, peptides, peptide aptamers) can covalently conjugate to and stably encapsulated in, forming nano-assemblies, and be controllably delivered and released (e.g., tracelessly) upon degradation of the nano-structures in response to specific microenvironment, and compositions and methods of preparation and use thereof.

In one aspect, the invention generally relates to a polymer-protein conjugate comprising a protein covalently conjugated to a polymer, wherein the polymer-protein conjugate is formed by one or more reactions between one or more side chain functionalities of the polymer and one or more surface-exposed functional groups of one or more lysine residues of the protein, leading to covalent capture and organization of the polymer around the protein.

In another embodiments, the invention generally relates to a nano-assembly comprising a polymer-protein conjugate wherein the protein is encapsulated in and covalently conjugated to a crosslinked polymer nextwork, wherein the crosslinked polymer network is de-crosslinkable thereby releasing the protein. In preferred embodiments, the polymer-protein conjugate is formed by one or more reactions between one or more side chain functionalities of the polymer and one or more surface-exposed functional groups of one or more lysines of the protein, leading to covalent capture and organization of the polymer around the protein.

In yet another aspect, the invention generally relates to a composition comprising a nano-assembly disclosed herein. In certain embodiments, the composition further includes a pharmaceutically acceptable excipient, carrier or diluent.

In yet another aspect, the invention generally relates to a crosslinked polymer network disclosed herein, for example, a crosslinked polymer network comprising structural units of:

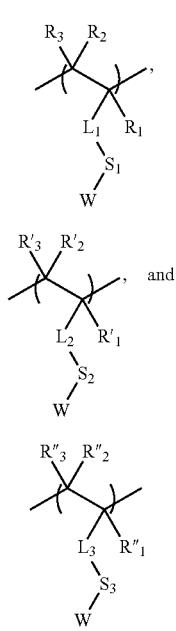

(I), (II), (III)

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a group comprising a zwitterionic group;
X is a group comprising a disulfide bond; and
Y is a group comprising a hydrophilic group,
as defined herein.

In yet another aspect, the invention generally relates to a composition comprising crosslinked polymer network disclosed herein. In certain embodiments, a protein encapsulated in and covalently conjugated to the crosslinked polymer nextwork.

In yet another aspect, the invention generally relates to a kit comprising a polymer and a crosslinking reagent, wherein the polymer is reactive to a protein to form a polymer-protein conjugate by one or more reactions between one or more side chain functionalities of the polymer and one or more surface-exposed functional groups of one or more lysine residues of the protein, leading to covalent capture and organization of the polymer around the protein.

In yet another aspect, the invention generally relates to a kit comprising a polymer, a protein, and a crosslinking reagent, wherein the polymer and the protein are capable of forming a polymer-protein conjugate by one or more reactions between one or more side chain functionalities of the polymer and one or more surface-exposed functional groups of one or more lysine residues of the protein, leading to covalent capture and organization of the polymer around the protein.

In yet another aspect, the invention generally relates to a polymer comprising structural units of:

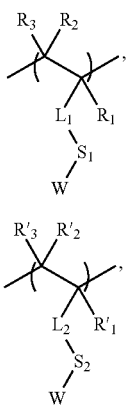

(I), (II)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, ($C_1$-$C_{16}$) alkyl, ($C_1$-$C_{16}$) alkyloxy, or halogen;
each of $L_1$ and $L_2$ is independently a linking group;
each of $S_1$ and $S_2$ is independently a single bond or a spacer group;
W is a group comprising a hydrophobic group; and
X is a group comprising a disulfide bond linked to a —O—(C=O)—O—$R_x$, wherein $R_x$ is selected from:

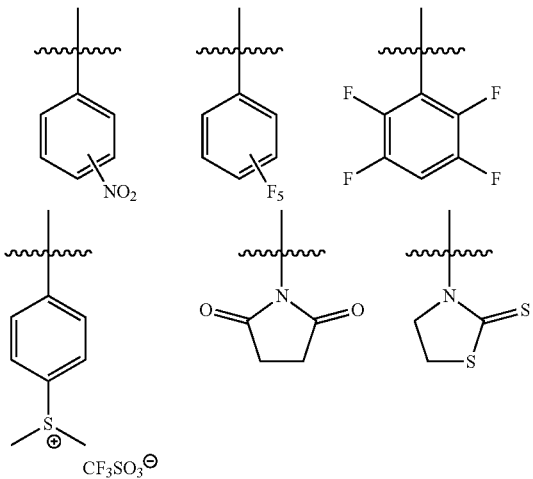

In yet another aspect, the invention generally relates to a method for treating a disease or condition. The method includes administering to a subject in need thereof a therapeutically effective amount of a composition disclosed herein.

In yet another aspect, the invention generally relates to a method for controlled delivery of a protein to a target biological site inside a cell. The method includes: providing a nano-assembly comprising a polymer-protein conjugate wherein the protein is encapsulated in and covalently conjugated to a crosslinked polymer nextwork; delivering the nano-assembly intracellularly to the target biological site; and causing at least partial dissociation of the nano-assembly and release of the protein therefrom resulting in intracellular release of the protein at the target biological site. In preferred embodiments, the nano-assembly is formed by reacting one or more side chain functionalities of the polymer with one or more surface-exposed functional groups of one or more lysine residues of the protein; and encapsulating the protein of the polymer-protein conjugate by forming a crosslinked polymer network around the conjugated protein.

BRIEF DESCRIPTION OF THE DRAWINGS

FIG. 1A. Schematic representation of the formation of a covalent polymer network using the protein as the template and its traceless and triggered release in a reducing environment.

FIG. 1B. Scheme 1. Chemical structures of polymers and the reaction scheme for protein conjugation, crosslinking to generate the nanoassembly and its release in the presence of a reducing agent.

FIG. 2. (a) TEM image of the clustered NA-CytC$^{PEG}$ particles, with the zoom-in of one of the particles in the inset. (b) MALDI-MS analysis of the trypsin digest from the encapsulated and naked CytC; (c, d) SDS-PAGE of the NA-CytC$^{PEG}$ under non-reducing and reducing conditions.

FIG. 3. Structure and function of released CytC from the NA-CytC$^{PEG}$, evaluated by (a) circular dichroism (CD); and (b-c) ABTS activity assay.

FIG. 4. HeLa cells treated with NA-CytC$^{PEG}$ conjugates to study cellular uptake: (a) 4 h post-incubation; (b-c) endosomal co-localization and escape at 4 h and 24 h, respectively; (green: lysotracker; red: rhodamine B; blue: hoechst); (d) cell viability (after 72 h); (e) detection of activated caspase-3/7 after 72 h using the Cy5 reagent; scale bar: (a) 50 μm, (b, c, e) 10 μm.

FIG. 5. SDS-PAGE showing protein release (under reducing conditions), cellular uptake (4 h) and viability (72 h) in HeLa cells for (a) NA-Lys and (b) NA-RNaseA conjugates, scale bar: 50 μm.

FIG. 6. $^1$H-NMR spectra of p(PEGMA-co-PDSMA), $P_{PcP}$.

FIG. 7. $^1$H-NMR spectra of p(PEGMA-co-EDSMA), $P_{PcE}$.

FIG. 8. $^1$H-NMR spectra of p(PEGMA-co-NPC), P1.

FIG. 9. GPC(THF) for polymers $P_{PcP}$, $P_{PcE}$ and P1.

FIG. 10. (a) Time-course of absorbance profile for released 4-nitrophenol as a fate of conjugation of lysozyme with polymer P1; Absorbance spectra of polymer-protein conjugates-before and after crosslinking for (b) lysozyme; (c) RNase A and (d) cytochrome C. UV-visible absorption spectra were recorded on a PerkinElmer Lambda 35 spectrophotometer.

FIG. 11. Particle size analysis of protein-polymer nanoassemblies from DLS measurements.

FIG. 12. Zeta potential plots for protein-polymer nanoassemblies.

FIG. 13. TEM images for ED and PEG-crosslinked PPCs.

FIG. 14. EDX profile indicating Fe content inside NA-CytC$^{PEG}$ conjugates: (a, b) inside particle and (c) outside particle.

FIG. 15. Trypsin digest for ED and PEG-crosslinked polymer-protein nanoassemblies.

FIG. 16. Particle size analysis of nanoassemblies in presence of serum.

FIG. 17. Lysine residues in Lysozyme (#6), RNase A (#10) and Cytochrome C (#19).

FIG. 18. SDS-PAGE for encapsulation analysis with nanoassemblies containing Lys and RNaseA.

FIG. 19. Release kinetics of proteins from the nanoassemblies by SDS-PAGE at disulfide of polymer to DTT ratio 1:1.

FIG. 20. Release kinetics of proteins from the PPCs by SDS-PAGE at disulfide of polymer to DTT ratio 1:10, quantification data provided in the 3D bar graph after 6 h of release.

FIG. 21. Release kinetics of proteins from the nanoassemblies.

FIG. 22. Activity of released proteins from nanoassemblies containing (a-b) Lysozyme; (c-d) RNase A.

FIG. 23. CD spectra of native proteins and polymer-protein nanoassemblies.

FIG. 24. Comparison of MALDI-MS spectra of the native proteins and released proteins from nanoassemblies.

FIG. 25. Negligible uptake for HeLa cells incubated with only proteins, cell nucleus was stained with Hoechst 33342, scale bar: 50 μm.

FIG. 26. Cellular internalization with ED-crosslinkied nanoassemblies, cell nucleus was stained with Hoechst 33342, scale bar: 50 μm.

FIG. 27. (a) Depth profiling for NA-CytC$^{PEG}$ dosed nanoassemblies: pseudo-colored consecutive slices through z-axis and (b) z-stack orthogonal projection from CLSM experiment showing localization of cytochrome C inside HeLa cells.

FIG. 28. (a) Time course of uptake for NA-CytC$^{PEG}$, (b) Fluorescence intensity measurement from the red channel by Image J software at different time points of uptake experiment, expressed as Corrected total cell fluorescence, CTCF=Integrated Density−(Area of selected cell×Mean fluorescence of background).

FIG. 29. Endosomal escape studies by co-localization of LysoTracker Green and Rhodamine B tagged protein; co-localization of dyes after 4 h incubation confirms existence in the endosomes and after 24 h distinct red fluorescence confirms release of proteins into the cytosol from endosomes. Scale bar: 10 μm.

FIG. 30. Detection of activated caspase-3/7 after 72 h in control HeLa cells treated with NA-Empty$^{PEG}$ sample; scale bar: 10 μm, no co-localization of hoechst and cy5-tagged assay reagent was observed in the nucleus.

FIG. 31. Toxicity from small molecule byproducts. Upon encountering the GSH-stimulus, the polymer-protein complex will degrade to form two byproducts. These data show that both of these by products are not cytotoxic to HeLa cells.

FIG. 32. Toxicity from small molecule byproducts. Upon encountering the GSH-stimulus, the polymer-protein complex will degrade to form two byproducts. These data show that both of these by products are not cytotoxic to DU-145 cells.

FIG. 33. Toxicity from small molecule byproducts. Upon encountering the GSH-stimulus, the polymer-protein complex will degrade to form two byproducts. These data show that both of these by products are not cytotoxic to 293T cells.

FIG. 34. Cellular uptake of NA-CC-PEG (Rhodamine tagged Cytochrome C) in DU-145 cell lines.

FIG. 35. Cellular uptake of NA-CC-PEG (Rhodamine tagged Cytochrome C) in 293T cell lines.

FIG. 36. Evaluation of uptake pathways using pathway inhibitors. The major forms of uptake for the Cytochrome C-incorporated polymer nanoassembly are macropinocytosis and clathrin mediated endocytosis.

FIG. 37. Crosslinking with 1, 4 and 10 eqv. of diamine (secondary crosslinker) was examined to test the control over protein release. With increasing secondary crosslink density, the release kinetics became slower reflected by the time dependent release studies.

FIG. 38. Exemplary polymer crosslinking using disulfide a crosslinker.

DETAILED DESCRIPTION OF THE INVENTION

The invention provides a novel strategy involving the protein-templated polymer self-assembly for the formation of a polymer network around the proteins and then tracelessly releasing them inside the cell. The demonstrated versatility of the approach indicates that the strategy is compatible with a wide array of biologics.

The present invention is based on a covalent self-assembly approach, where the protein cargo itself acts as the template for the polymer to self-assemble around it. This novel platform allows encapsulation of proteins with high fidelity and present charge-neutral surface functionalities (FIG. 1A).

A key design feature is that an initial reaction between the side chain functionalities of a random copolymer and multiple surface-exposed functional groups of a target protein causes a few polymer chains to organize around the protein. As disclosed herein, this covalent capture then can act as a template to form a polymer network around the protein through a polymer side-chain crosslinking step, as schematically illustrated in FIG. 1A. The high-fidelity protein encapsulation within this polymer network may be aided by: (a) convex surface of globular proteins on which the reactive functional groups are presented; and (b) high-yielding and multivalent reactions between the protein and polymer side chains.

Cysteine and lysine are two popular handles for conjugating polymers with proteins, because of their nucleophilicity. (Stenzel 2013 *ACS Macro Lett.* 2, 14; Hoyle, et al. 2010 *Angew. Chem. Int. Ed.* 49, 1540; Chen, et al. 1990 *Biomaterials* 11, 625; Ventura, et al. 2015 *Biomacromolecules* 16, 3161; Vazquez-Dorbatt, et al. 2009 *Macromolecules* 42, 7650; Wiss, et al. 2009 *Macromolecules* 42, 3860; Li, et al. 2011 *Polym. Chem.* 2, 323; Danial, et al. 2014 *J. Am. Chem. Soc.* 136, 8018.) Because of the surface availability of multiple lysines in larger number of proteins, lysines are preferred.

Lysines, however, present a disadvantage in that it is more difficult to functionalize lysines, whereby they can be tracelessly liberated in the presence of an intra-cellular environment. As disclosed herein, by placing reactive side-chain functionalities, complementary to amines, with responsive self-immolation characteristics in a polymer provides a novel and general system that is capable of encapsulating proteins with high fidelity and tracelessly releasing them upon encountering a target microenvironment. (Riber, et al. 2015 *Adv. Healthcare Mater.* 4, 1887.)

By "traceless" release as used herein is meant that the released agent (e.g., protein) does not include any traces of a linker or vehicle (e.g., polymer).

Scheme 1 (FIG. 1B) shows the structure of polymer P1, which satisfies all the design requirements. Reaction of an amine with the p-nitrophenylcarbonate moiety in P1 produces the corresponding carbamate, shown in P2. The polymer is first treated with the protein, where multiple lysine moieties are reacted with the p-nitrophenylcarbonate groups in the polymer chains. Following this, the remaining carbonate moieties are reacted with a diamine crosslinker to complete the polymer network formation around the protein, as represented in FIG. 1A and FIG. 1B (Scheme 1).

Note that a disulfide moiety is placed at the beta-position, relative to the carbamate oxygen. The purpose of this placement is to render the polymer responsive to the more reductive environment present inside the cells, compared to the extracellular environment. Reductive cleavage of the disulfide moiety will result in the thiol intramolecularly cleaving the carbamate moiety to release the original amine. This reaction causes both the polymer being uncrosslinked and the protein being tracelessly liberated from the polymer.

To test this design strategy, cytochrome C (CytC, pI 9.6) was chosen as a model protein, because of its distinct cellular readout in the form of apoptotic cell death. After initially reacting CytC with P1, the polymer-protein conjugate was further secured by crosslinking with ethylenediamine (ED) or tetraethyleneoxide-bis-amine (PEG) to afford nanoassemblies NA-CytC$^{ED}$ and NA-CytC$^{PEG}$, respectively. Note that the reaction between the p-nitrophenylcarbonate moiety and an amine produces p-nitrophenol as a by-product, the distinct absorption of which is conveniently monitored with spectrophotometry. Therefore, the protein conjugation step was quantified using the evolution of the absorption spectrum (FIG. 10).

The encapsulation efficiency and loading capacity were found to be ~47% and 5-7%, respectively. Dynamic light scattering (DLS) measurements revealed the hydrodynamic diameters of native CytC and the protein-containing nano-assembly to be ~4 nm and ~8-10 nm, respectively (FIGS. 11 and 12). Moreover, zeta potential measurements revealed that the surface of the complex is charge-neutral, indicating that the complex surface is dominated by the PEG moieties from P1. Next, these complexes were imaged using transmission electron microscopy (TEM) (FIG. 2). The unstained images show a soft core, presumably indicating the presence of a hydrated core. Although the assembly's core was stable enough to withstand high vacuum employed during analysis, they coalesced with surrounding particle-cores when focused with high energy TEM electron beam. This coalescence leads to the image of a multi-compartmental nanoassembly (NA) seen in FIG. 2. To investigate whether CytC is indeed present in these assemblies, energy-dispersive x-ray (EDX) analysis of the complex also confirmed the presence of Fe inside the observed particles. (FIG. 14).

An important feature of this disclosed platform is the use of the polymer network to protect the protein from protease degradation. To rigorously test for this, the polymer-protein conjugate was subjected to protease digest with trypsin and analyzed the products using matrix-assisted laser desorption/ionization mass spectrometry (MALDI-MS). While the unprotected native CytC afforded characteristic peptide fragment peaks, the conjugate at the same protein concentration did not afford any discernible peptide fragments (FIG. 2). These results showed that assemblies do indeed protect the caged protein. The conjugates also were observed to be generally stable in serum (FIG. 16).

Next studies focused on evaluating whether the encapsulated protein can be released in a reducing environment. First this possibility was tested using gel electrophoresis (SDS-PAGE). As anticipated, when the protein is conjugated to the protein, no bands corresponding to the protein was found (FIG. 2). When the same SDS-PAGE gel was run under reducing conditions, appearance of protein bands clearly indicated that the encapsulated protein can be released. This is the first evidence that the protein release using the reductive self-immolative linker is feasible. SDS-PAGE experiments were utilized to quantify the amount of proteins inside the nanoassemblies. After treating the nano-assemblies with excess dithiothreitol (DTT), the intensity of the protein band in the gel is compared with native proteins of different concentrations to estimate the amount of proteins present inside the nanoassembly (FIG. 2).

The protein encapsulation and release process would be a futile exercise, if the methodology does not preserve the structure and function of the protein upon release. To this end, the secondary structure of the released protein was examined by circular dichroism (CD) spectroscopy, the spectrum of which was found to be identical to that of the native CytC (FIG. 3). This indicates that the conjugation and release processes did not alter the secondary structure of the protein.

To test whether the strategy leads to a traceless release of the protein in reductive environment, the released protein was analyzed by mass spectrometry. The m/z for the released protein matched the native CytC, indicating that there are no remnants of the polymer after the protein's reductive release (FIG. 24).

Next studied was whether the function of the protein is maintained by quantifying the released protein's activity using an ABTS assay (based on 2,2'-azino-bis(3-ethylbenzthiazoline-6-sulfonic acid) (FIG. 3b-c). (Childs, et al. 1975 Biochem. J. 145, 93.) While the nanoassembly did not exhibit any enzymatic activity, the activity recovery was nearly quantitative when the assembly was treated with 10 mM DTT (compare the activities of native CytC and released CytC in the presence of 10 mM DTT in FIG. 3). This activity recovery was also found to be dependent on the concentration of DTT and thus the extent of protein release. These results show that the polymer shell can act to 'turn-off' the protein function, until it is released in its target environment. Both structure and function recoveries were found to be independent of the crosslinker length in ED and PEG linkers, as shown in FIG. 3.

The ultimate goal of the proposed research is to utilize this polymer coating to traffic the protein across the cellular membrane and release it in the cytosol. It is the higher redox potential of the cytosol that is being targeted for selective release. To track the location of the protein under confocal laser scanning microscopy (CLSM), CytC was labeled with rhodamine B and the cell nucleus was stained with hoechst 33342. After 4 h incubation, well-distributed red fluorescence from labeled proteins was observed (FIG. 4a), while negligible fluorescence was observed from cells that were treated with an identical concentration of naked proteins (FIG. 25). These results indicate that the polymer conjugate has better access to the cells, compared to the native protein itself. The time course of cellular internalization process was also monitored under CLSM for this conjugate (FIG. 28). Since the most likely pathway for uptake is endosomal escape, next evaluated was whether the proteins are stuck in the endosome or they escaped the endosome to get into the cytosol. For a cytosolic delivery, the latter is desired. Accordingly, the endosomes were labeled with lysotracker green. The data clearly indicate that the nanoassemblies enter the cells through the endosomes (see co-localization of lysotracker green and rhodamine-B label after 4 h incubation (FIG. 4b)), but the proteins escape the endosomes over time as seen by the dominant red color in the cell in the 24 h image (FIG. 4c).

To evaluate whether the delivered CytC is active, the apoptotic cell death in response to the protein delivery was evaluated. CytC is known to induce apoptosis through interaction with apoptotic protease activating factor 1 (Apaf-1) in cytosol and activation of pro-caspase-9, which in turn initiates pro-caspase-3 leading to activation of caspase dependent apoptotic pathways. (Santra, et al. 2010 Mol. Pharmaceutics 7, 1209. (c) Morales-Cruz, et al. 2014 J. Nanobiotechnol. 12:33.) The dose-dependent decrease in cell viability of the nanoassembly, combined with the lack of toxicity for the corresponding concentration of the free nanoassembly or naked CytC, indicate that the cytosolically delivered CytC is causing apoptosis.

Furthermore, the mechanism of action of CytC allows the direct interrogation whether the caspase-dependent pathway is activated in the cytosol. A fluorimetric immunoassay that causes a caspase product to be intercalated the DNA in the nucleus was utilized to asses this possibility. The co-localization of the caspase-processes, cy5-tagged reagent (red) and the nuclear stain (blue) confirmed the apoptotic nuclei in the cells (FIG. 4e). Control experiments show that the nanoassembly without the CytC does not cause the activation of the cy5-tagged reagent.

The true testament to the versatility of this strategy is the applicability to a broad range of proteins. Two other proteins, viz. lysozyme (Lys) and ribonuclease A (RNaseA) were tested. Both proteins were found to be successfully conjugated with the polymer P1. SDS-PAGE, CD, and activity studies also show that the encapsulated protein can be released with high fidelity under reducing conditions with high retention in both structure and function (FIG. 4a-b). It is interesting to note that the overall kinetics of proteins release was observed to have the order: CytC<RNaseA<Lys. The release kinetics seems to correlate with the number of surface exposed lysines in each protein (CytC: 19, RNaseA: 10, Lys: 6). (Prasanna Murthy, et al. 2009 Biochemistry 48, 2654; Bosshard, et al. 1980 J. Biol. Chem. 255, 6694.) This is understandable, since the higher number of anchoring points requires more sites for the reducing agent to process during release.

Finally, the intracellular delivery and activity of these proteins were also evaluated (FIG. 5). While lysozyme is expected to be innocuous to cells, RNaseA with access to cytosolic RNA can initiate cell death. (Wang, et al. 2014 Angew. Chem. Int. Ed. 53, 13444. (b) Ellis, et al. 2012 J. Am. Chem. Soc. 134, 3631.) Although both proteins were taken up by the cells as assessed by CLSM studies, the lysosome-containing nanoassembly did not induce any cell-kill, whereas the RNaseA-bearing nanoassembly had a profound effect on cell viability (FIG. 5).

Thus, in one aspect, the invention generally relates to a polymer-protein conjugate comprising a protein covalently conjugated to a polymer, wherein the polymer-protein conjugate is formed by one or more reactions between one or more side chain functionalities of the polymer and one or more surface-exposed functional groups of one or more lysine residues of the protein, leading to covalent capture and organization of the polymer around the protein.

In another aspect, the invention generally relates to a nano-assembly comprising a polymer-protein conjugate wherein the protein is encapsulated in and covalently conjugated to a crosslinked polymer nextwork, wherein the crosslinked polymer network is de-crosslinkable thereby releasing the protein. In preferred embodiments, the polymer-protein conjugate is formed by one or more reactions between one or more side chain functionalities of the polymer and one or more surface-exposed functional groups of one or more lysines of the protein, leading to covalent capture and organization of the polymer around the protein.

In certain embodiments, the polymer-protein conjugate or nano-assembly is adapted to stably transporting the protein across a cell membrane and then tracelessly releasing it in the cell.

In certain embodiments, the protein of the polymer-protein conjugate is encapsulated with crosslinking of the polymer, or optionally with another polymer, forming a crosslinked polymer network around the conjugated protein.

In certain embodiments, the crosslinked polymer network is crosslinked at least in part by one or more linkers having a disulfide bond.

In certain embodiments, the crosslinked polymer network is de-crosslinked in response to a specific microenvironment resulting in degradation of the nano-assembly and release of the protein in the cell (e.g., cytosol).

In certain embodiments, the crosslinked polymer network is decrosslinked and the protein is releasable in the cell (e.g., cytosol) triggered by an intracellular reducing environment (e.g., an elevated glutathione concentration).

In certain embodiments, the released protein is characterized by intact biological activity.

In certain embodiments, the one or more surface-exposed functional groups of the protein are selected from functional groups of lysine residue or cysteine residue. In certain embodiments, the functional groups of the proteins are from lysine.

As used herein, the term "protein" refers to a polypeptide, a polymer of amino acid residues, and is not limited to a minimum length. Thus, peptides, oligopeptides, dimers, multimers, enzymes, antibodies, aptamers and the like, are included within the definition. Both full-length proteins and fragments thereof are encompassed by the definition. The term also includes post-expression modifications of the polypeptide, for example, glycosylation, acetylation, phosphorylation, and the like. Furthermore, a "protein" may refer to a polypeptide which includes modifications, such as deletions, additions, and substitutions (generally conservative in nature), to the native sequence, as long as the protein maintains the desired activity. These modifications may be deliberate or may be accidental.

Any suitable biomolecules may be encapsulated and conjugated, for example, a protein is selected from the group consisting of cytosolic proteins bearing at least one lysine residue (e.g., one, one or more, two, two or more, or more than two, lysine residues) in their monomeric or aggregated form.

In certain embodiments, the protein is selected from the group consisting of intracellular proteins bearing at least two lysine residues in their monomeric or aggregated form.

In certain embodiments, the protein is selected from a fragment of an intracellular protein bearing at least two lysine residues in their monomeric or aggregated form.

In certain embodiments, the protein is based on a non-intracellular protein, from a natural source or made of an artificial amino acid sequence, bearing at least two lysine residues in their monomeric or aggregated form.

In certain embodiments, the protein comprises a mixture of natural and artificial amino acid sequence components in their monomeric or aggregated form.

In certain embodiments, the protein is a full-length antibody or a fragment of an antibody that is capable of binding to a target molecule inside the cell.

Any suitable polymers may be employed to form the nano-assembly. In certain embodiments, the polymer is a random copolymer. Any suitable polymers may be employed to form the nano-assembly. In certain embodiments, the polymer is a block copolymer.

In certain embodiments, the crosslinked polymer network comprises structural units of:

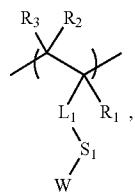
(I)

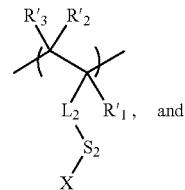
, and
(II)

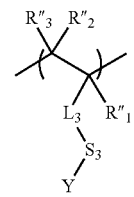
(III)

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a group comprising a zwitterionic group;
X is a group comprising a disulfide bond; and
Y is a group comprising a hydrophilic group.

In certain embodiments, each of $L_1$, $L_2$ and $L_3$ is independently selected from the group consisting of

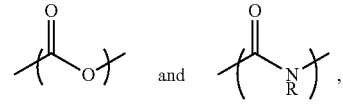

wherein R is H or a $C_1$-$C_6$ alkyl.

In certain embodiments, each of $S_1$, $S_2$ and $S_3$ is independently a single bond and a —$(CH_2)_m$—, wherein m is an integer from 1 to about 16.

In certain embodiments, W comprises a zwitterionic group selected from the group consisting of:

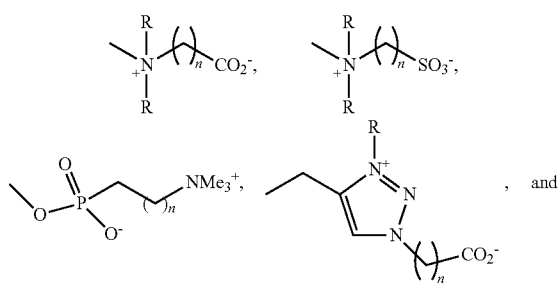

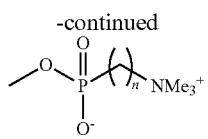

wherein each R is hydrogen or a $C_1$-$C_{15}$ alkyl group; n is independently an integer from about 1 to about 12.

In certain embodiments, Y comprises a —($CH_2CH_2$—O)$_p$— group, wherein p is an integer from about 1 to about 500.

In certain embodiments, Y comprises

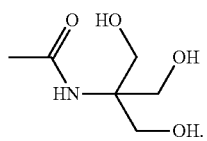

In certain embodiments, wherein X comprises —($CH_2$)$_m$—S—S—($CH_2$)$_n$— or —($CH_2CH_2$—O)$_m$—S—S—($CH_2CH_2$—O)$_n$—, wherein each of m and n is independently an integer from 1 to about 16.

In certain embodiments, X comprises a disulfide bond flanked on both sides by a group selected from —($CH_2$)$_i$— and —($CH_2CH_2$—O)$_j$—, wherein each of i and j is independently an integer from 1 to about 16.

In certain embodiments, X comprises a group selected from:

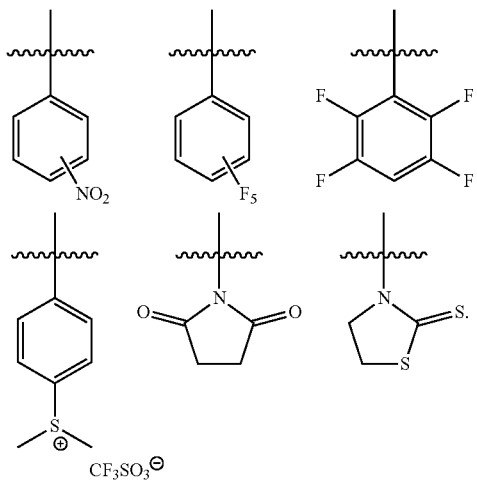

In certain embodiments, X comprises a linkage group of —O—(C=O)—O—.

In certain embodiments, each of $R_1$, $R'_1$ and $R''_1$ is methyl and each of $R_2$, $R'_2$, $R''_2$, $R_3$, $R'_3$ and $R''_3$ is H.

In certain embodiments, each of each of $L_1$, $L_2$ and $L_3$ is

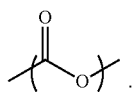

In certain embodiments, each of each of $L_1$, $L_2$ and $L_3$ is

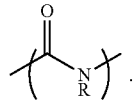

An exemplary polymer crosslinking scheme is shown in FIG. 38.

In another aspect, the invention generally relates to a composition comprising a nano-assembly disclosed herein.

In certain embodiments, the composition further includes a pharmaceutically acceptable excipient, carrier or dilutent.

In yet another aspect, the invention generally relates to a crosslinked polymer network disclosed herein, for example, a crosslinked polymer network comprising structural units of:

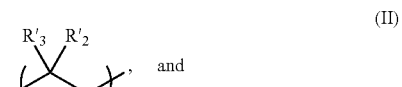

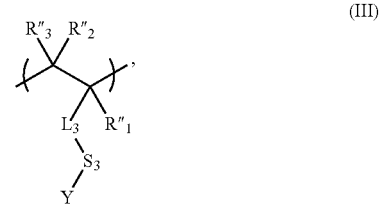

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a group comprising a zwitterionic group;
X is a group comprising a disulfide bond; and
Y is a group comprising a hydrophilic group,
as defined herein.

In yet another aspect, the invention generally relates to a composition comprising crosslinked polymer network disclosed herein. In certain embodiments, a protein encapsulated in and covalently conjugated to the crosslinked polymer nextwork.

In yet another aspect, the invention generally relates to a kit comprising a polymer and a crosslinking reagent, wherein the polymer is reactive to a protein to form a polymer-protein conjugate by one or more reactions between one or more side chain functionalities of the polymer and one or more surface-exposed functional groups of one or more lysine residues of the protein, leading to covalent capture and organization of the polymer around the protein.

In yet another aspect, the invention generally relates to a kit comprising a polymer, a protein, and a crosslinking reagent, wherein the polymer and the protein are capable of forming a polymer-protein conjugate by one or more reactions between one or more side chain functionalities of the polymer and one or more surface-exposed functional groups of one or more lysine residues of the protein, leading to covalent capture and organization of the polymer around the protein.

In certain embodiments, the kit further includes a buffer.

In certain embodiments, the protein is provided in a buffer.

In certain embodiments, the polymer is further capable of crosslinking with the crosslinking reagent to form a crosslinked polymer nextwork with the protein encapsulated therein and covalently conjugated thereto; and the crosslinked polymer network is de-crosslinkable thereby releasing the protein.

In certain embodiments, the crosslinker comprises a disulfide bond.

In yet another aspect, the invention generally relates to a polymer comprising structural units of:

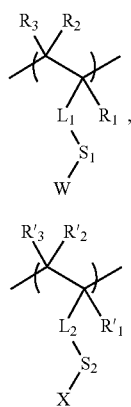

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, ($C_1$-$C_{16}$) alkyl, ($C_1$-$C_{16}$) alkyloxy, or halogen;
each of $L_1$ and $L_2$ is independently a linking group;
each of $S_1$ and $S_2$ is independently a single bond or a spacer group;
W is a group comprising a hydrophobic group; and
X is a group comprising a disulfide bond linked to a —O—(C=O)—O—$R_x$, wherein $R_x$ is selected from:

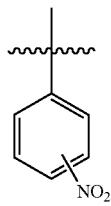 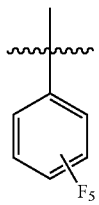 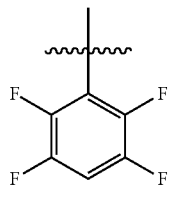

-continued

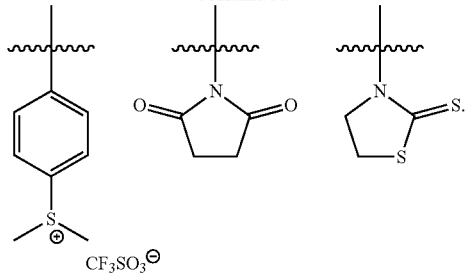

In certain embodiments, each of $L_1$ and $L_2$ is independently selected from the group consisting of

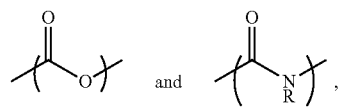

wherein R is H or a $C_1$-$C_6$ alkyl.

In certain embodiments, each of $S_1$ and $S_2$ is independently a single bond and a —$(CH_2)_m$—, wherein m is an integer from 1 to about 16.

In certain embodiments, W comprises a zwitterionic group selected from the group consisting of:

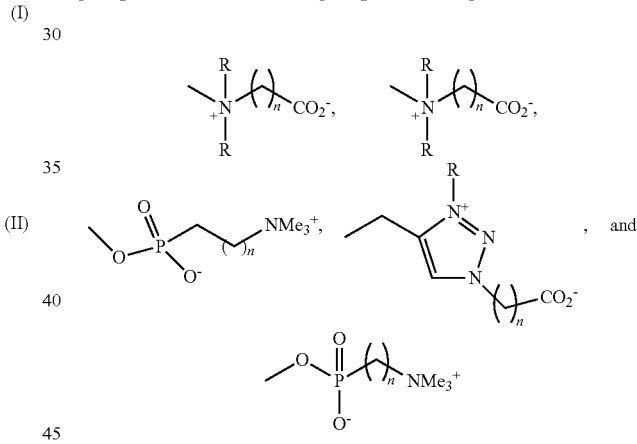

wherein each R is hydrogen or a $C_1$-$C_{15}$ alkyl group; n is independently an integer from about 1 to about 12.

In certain embodiments, each of $R_1$=$R'_1$=methyl and each of $R_2$, $R'_2$, $R_3$ and $R'_3$ is H.

In yet another aspect, the invention generally relates to a method for treating a disease or condition. The method includes administering to a subject in need thereof a therapeutically effective amount of a composition disclosed herein.

In yet another aspect, the invention generally relates to a method for controlled delivery of a protein to a target biological site inside a cell. The method includes: providing a nano-assembly comprising a polymer-protein conjugate wherein the protein is encapsulated in and covalently conjugated to a crosslinked polymer nextwork; delivering the nano-assembly intracellularly to the target biological site; and causing at least partial dissociation of the nano-assembly and release of the protein therefrom resulting in intracellular release of the protein at the target biological site. In preferred embodiments, the nano-assembly is formed by reacting one or more side chain functionalities of the polymer with one or more surface-exposed functional groups of one or more lysine residues of the protein; and encapsulating the protein of the polymer-protein conjugate by forming a crosslinked polymer network around the conjugated protein.

In certain embodiments, the partial or complete dissociation of the nano-assembly is by decrosslinking of the crosslinked polymer network thereby releasing the protein.

In certain embodiments, the protein is a cytosolically active protein.

In certain embodiments, the crosslinked polymer network is de-crosslinked in response to a specific microenvironment resulting in degradation of the nano-assembly and release of the protein.

In certain embodiments, the crosslinked polymer network is decrosslinked and the protein is releasable in the cytosol triggered by an intracellular reducing environment (e.g., an elevated glutathione concentration).

In certain embodiments, the released protein is biologically active.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butylenegly-col, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C, et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In summary, a versatile strategy for the encapsulation of proteins and their traceless release in response to a specific trigger is demonstrated. The encapsulation is templated by the lysine handles in the protein itself, which are then used to wrap the protein with a polymer network in a secondary crosslinking step. The versatility of the approach is highlighted by the fact that: (i) it utilizes a functional handle that is abundantly available on the surface of >85% the globular proteins, which renders the strategy broadly applicable; (ii) the target protein is encapsulated with high fidelity, i.e. high loading capacity; (iii) the cargo is protected from degradation by proteases; (iv) the protein activity is masked in the encapsulated state; (iv) the polymer network is removed tracelessly with high efficiency in response to a target intracellular environment; (v) the native structure and function are retained upon release; (vi) the protein can be delivered with high fidelity into the cytosol; and (vii) activity of the protein is regained in the cytosol. Thus, this simple yet generally applicable strategy can serve to produce a potent protein therapeutic delivery platform for a broad range of proteins.

EXPERIMENTAL

Materials

All chemicals, polyethylene glycol monomethyl ether methacrylate (PEGMA; MW 500), 2,2'-dithiodipyridine, 4-cyano-4-(phenylcarbonothioylthio)pentanoic acid (chain transfer agent), D,L-dithiothreitol (DTT), lysozyme, RNase A, cytochrome C and rhodamine B isothiocyanate were obtained from Sigma-Aldrich and were used without further purification unless otherwise mentioned. 2,2'-azobis-(2-methylpropionitrile) (AIBN) was procured from Sigma-Aldrich and purified by recrystallization before usage. Pyridyl disulfide ethyl methacrylate (PDSMA) was synthesized using previously reported procedure.[i]

Synthesis of p(PEGMA-co-PDSMA), $P_{PcP}$

PDSMA (0.511 g, 2 mmol), PEGMA (1 g, 2 mmol) and 4-cyano-4-(phenylcarbonothioylthio) pentanoic acid (55.7 mg, 0.2 mmol) were weighed and dissolved with 2 mL THF in a 25 mL Schlenk flask. To the reaction mixture, 1 mL AIBN (6.7 mg, 0.0408 mmol) solution in THF was added and mixed for 5 min. The flask was purged with argon and performed three freeze-pump-thaw cycles. After that the reaction vessel was sealed and transferred to an oil bath preheated at 70° C. The polymerization was quenched after 24 h by cooling down the reaction flask with cold water and the solvent was evaporated. The viscous reaction product was purified by repeated washing with cold diethyl ether and finally dried in high vacuum at room temperature for 24 h. Yield: 96%, GPC (THF) $M_n$: 27 K. Đ: 1.1. $^1$H NMR (400 MHz, CDCl$_3$): δ 8.47, 7.70, 7.13, 4.21-4.07, 3.64-3.37, 3.03, 1.93-1.82, 1.03-0.87. From $^1$H NMR, integration of the methoxy proton (in PEG unit) and the aromatic proton (in pyridine unit) provided the molar ratio of two monomers to be 1:1 (PEG/PDS).

Modification of Synthesized p(PEGMA-co-EDSMA) Polymer, $P_{PcE}$

PDS polymer (1 g, 1.32 mmol PDS repeat unit) was weighed in a 20 mL glass vial and dissolved in 8 mL DCM. Catalytic amount (100 µL) of glacial AcOH was added to it and stirred for 5 min. Afterwards, 2-mercaptoethanol (0.9 mL, 13 mmol) was added dropwise to the reaction mixture and the solution was stirred for 24 h at room temperature. After that, the modified polymer was purified by dialyzing against methanol using a membrane of MWCO: 3.5 kDa. After dialysis, the solvent was evaporated and the polymer was dried under vacuum for 24 h. Yield: 90%, GPC (THF) $M_n$: 26 K. Đ: 1.2. $^1$H NMR (400 MHz, CDCl$_3$): δ 4.24-4.09, 3.87, 3.65-3.53, 3.37, 2.95-2.90, 1.93-1.84, 1.04-0.89.

Synthesis of p(PEGMA-co-NPC) (NPC: p-Nitrophenylcarbonate), P1

Modified polymer P2 (1 g, 1.39 mmol) and 4-Nitrophenyl chloroformate (325 mg, 1.61 mmol) were dissolved in 5 mL DCM taken in a 20 mL glass vial. The reaction mixture was cooled in ice bath for 10 min. To the cold mixture, pyridine (130 µL, 1.61 mmol) was added dropwise under vigorous stirring. Finally, the reaction mixture was stirred at room temperature for 24 h and the self-immolative polymer was purified by dialyzing against DCM/MeOH 1:1 mixture using a MWCO 3.5 kDa membrane. Yield: 98%, GPC (THF) $M_n$: 32 K. Đ: 1.2. $^1$H NMR (400 MHz, CDCl$_3$): δ 8.29-8.27, 7.41-7.42, 4.54, 4.23-4.08, 3.63-3.37, 3.04-2.94, 1.89-1.80, 1.03-0.88.

$^1$H-NMR Spectra for Polymer Samples $P_{PcP}$, $P_{PcE}$ and P1

$^1$H-NMR spectra of the samples were recorded on a 400 MHz Bruker NMR spectrometer using residual proton resonance of the solvent as the internal standard and chemical shifts were reported in parts per million (ppm).

Gel Permeation Chromatography (GPC) for $P_{PcP}$, $P_{PcE}$ and P1

Molecular weights of all synthesized polymers were estimated by GPC in THF using poly(methyl methacrylate) (PMMA) standards with a refractive index detector.

Synthesis of Polymer-Protein Nanoassemblies

NA-Empty$^{ED}$ and NA-Empty$^{PEG}$

The self-immolative polymer P1 (10 mg) was dissolved in 2.5 mL phosphate buffer (adjusted to pH 8.5) at 20° C. A calculated amount of ethylenediamine (for NA-Empty$^{ED}$) or (PEO)$_4$-bis-amine (for NA-Empty$^{PEG}$) was added to the solution and kept stirring for 24 h for cross-linking. The resulting nanoassembly was purified by repeated washing (5× times) with phosphate buffer pH 7.4 Amicon Ultra Centrifugal Filters MWCO 30K. The final volume of empty nanoassembly was adjusted to 500 µL with phosphate buffer of pH 7.4.

NA-Lys$^{ED}$, NA-Lys$^{PEG}$, NA-RNaseA$^{ED}$, NA-RNaseA$^{PEG}$, NA-CytC$^{ED}$ and NA-CytC$^{PEG}$ Initially, polymer P1 (10 mg) was dissolved in 1.5 mL phosphate buffer (adjusted to pH 8.5). To this solution, 1 mL solution of a specific protein (1 mg lysozyme or RNase A or cytochrome C in phosphate buffer, pH 8.5) was added dropwise and stirred for 24 h at 20° C. to generate P2. Then, calculated amount of ethylenediamine (for NA-Protein$^{ED}$) or (PEO)$_4$-bis-amine (for NA-Protein$^{PEG}$) was added to each solution for cross-linking and mixed for another 24 h at 20° C. Finally, the reaction mixture was washed (5× times) with phosphate buffer (pH 7.4) using Amicon Ultra Centrifugal Filters MWCO 30K to get purified nanoassemblies (NA) encapsulated with proteins. The final volume of all conjugates was adjusted to 500 µL with phosphate buffer of pH 7.4.

Monitoring Protein-Polymer Conjugation and Determination of Crosslinking Density The conjugation process and cross-linking density for the protein-polymer conjugates can be evaluated by UV-Vis spectroscopy. The amount of released 4-nitrophenol was monitored at its $\lambda$max 400 nm (measured molar extinction co-efficient$\approx$12.14*$10^3$ L $M^{-1}$ $cm^{-1}$ at 400 nm). For each absorbance measurement, samples were diluted to twenty times, for e.g. 50 µL of sample was diluted 1 mL with distilled water. Cross-linking density was calculated by assuming that formation of a single chain crosslinking bond would require cleavage of two NPC units and produce two 4-nitrophenol molecules.

Ratio of NPC:PEG in the polymer, P1=50:50
Molecular weight of repeating NPC-unit=387 g/mol
Amount of polymer used=0.1 mg/mL for each absorbance measurement
Moles of NPC-unit in the solution=(0.08*0.5/387)/1000=1.29*$10^{-7}$ mol
Example for NA-$Lys^{ED}$:
From Beer-lamber's law: A=$\varepsilon$.c.1 and path-length=1 cm
So, concentration of 4-nitrophenol c=0.3692/(12.14*$10^3$)=3.04*$10^{-5}$ M
Thus, moles of 4-nitro phenol in 1 mL solution=3.04*$10^{-8}$ This represents is 23.5 mol % of total NPC unit. As it is assumed that two 4-nitro phenol are released per crosslinking bond formation and NPC unit is 50 mol % of total polymer. Therefore, crosslinking density=23.5/2*0.5=5.9%

Hydrolysis from control polymer sample contributes ~1% towards cross-linking density and adjusted for all calculations. Crosslinking densities for all other conjugates were calculated based on the above method and summarized below:

TABLE 1

Crosslinking density of nanoassemblies

| Sample | Absorbance (at 400 nm) | Crosslinking density, % |
|---|---|---|
| NA-$Lys^{ED}$ | 0.3692 | 4.9 |
| NA-$Lys^{PEG}$ | 0.4377 | 6.0 |
| NA-RNase$A^{ED}$ | 0.3847 | 5.1 |
| NA-RNase$A^{PEG}$ | 0.3821 | 5.1 |
| NA-$CytC^{ED}$ | 0.3417 | 4.4 |
| NA-$CytC^{PEG}$ | 0.3816 | 5.1 |

Encapsulation Efficacy and Loading Capacity

All nanoassemblies were evaluated for amount of protein encapsulation after conjugation and cross-linking process. Protein concentration in each sample was measured from the filtrate after crosslinking reaction and the amount of protein was back-calculated in the conjugate. An absorbance based assay (with Pierce™ 660 nm Protein Assay Reagent) was utilized to quantify the protein amount. The encapsulation efficiency (EE) and loading capacity (LC) were calculated based on the following formulas:

$$EE, \% = \left[\frac{\text{initial protein loaded} - \text{free ``unencapsulated'' protein}}{\text{initial protein loaded}}\right] \times 100$$

$$LC, \% = \left[\frac{\text{amount of ``encapsulated'' protein}}{\text{amount of polymer}}\right] \times 100$$

TABLE 2

Encapsulation efficiency and loading capacity of nanoassemblies

| Sample | Amount of protein encapsulated, µg (Initial dose = 1 mg) | Encapsulation efficiency (EE), % | Loading capacity (LC), % |
|---|---|---|---|
| NA-$Lys^{ED}$ | 550 | 45 | 5.5 |
| NA-$Lys^{PEG}$ | 560 | 44 | 5.6 |
| NA-RNase$A^{ED}$ | 558 | 44 | 5.6 |
| NA-RNase$A^{PEG}$ | 553 | 45 | 5.5 |
| NA-$CytC^{ED}$ | 524 | 48 | 6.4 |
| NA-$CytC^{PEG}$ | 543 | 46 | 6.7 |

DLS and Zeta Potential Plots:

Dynamic light scattering (DLS) and zeta potential measurements were performed using a Malvern Nanozetasizer-ZS. All samples were diluted with phosphate buffer pH 7.4 to adjust final concentration to 1 mg/mL.

TABLE 3

Particle size values for the nanoassemblies

| Sample | Size, nm |
|---|---|
| Lysozyme | 3.6 ± 0.4 |
| RNase A | 3.3 ± 0.2 |
| Cytochrome C | 4.3 ± 0.1 |
| NA-$Empty^{ED}$ | 9.7 ± 0.1 |
| NA-$Empty^{PEG}$ | 9.5 ± 0.1 |
| NA-$Lys^{ED}$ | 9.7 ± 0.2 |
| NA-$Lys^{PEG}$ | 9.4 ± 0.3 |
| NA-RNase$A^{ED}$ | 9.1 ± 0.1 |
| NA-RNase$A^{PEG}$ | 9.5 ± 0.1 |
| NA-$CytC^{ED}$ | 9.2 ± 0.2 |
| NA-$CytC^{PEG}$ | 8.6 ± 0.1 |

TABLE 4

Particle size and zeta potential values for the nanoassemblies

| Sample | Zeta potential, mV |
|---|---|
| NA-$Empty^{ED}$ | −7.3 ± 1.3 |
| NA-$Empty^{PEG}$ | −9.2 ± 1.5 |
| NA-$Lys^{ED}$ | −7.6 ± 0.7 |
| NA-$Lys^{PEG}$ | −7.1 ± 0.4 |
| NA-RNase$A^{ED}$ | −8.2 ± 0.7 |
| NA-RNase$A^{PEG}$ | −8.7 ± 0.7 |
| NA-$CytCE^{D}$ | −6.4 ± 0.5 |
| NA-$CytC^{PEG}$ | −2.1 ± 0.5 |

Calculation of Number of Proteins Per Particle:

Example for NA-$Lys^{ED}$:

Diameter of nanoassembly, D=9.7 nm, radius, R=4.85 nm

Volume of each particle, $V_{PPC}$=(4/3)$\pi R^3$=(4/3) $\pi(4.85)^3$ $nm^3$=477.6×$10^{-21}$ $cm^3$ Again, for lysozyme, diameter of protein, d=3.6 nm, radius, r=1.8 nm Volume of each protein, $V_{Ly}$=(4/3)$\pi r^3$=(4/3) $\pi(1.8)^3$ $nm^3$=24.4×$10^{-21}$ $cm^3$ Assuming that maximum sphere packing efficiency to be ~74%,[ii] number of lysozyme per nanoassembly to be= (477.6×$10^{-21}$/24.4×$10^{-21}$)×(0.74)=14

The results for all other nanoassemblies are summarized below:

TABLE 5

Number of proteins per nanoassembly

| Sample | # of Protein per PPC particle |
|---|---|
| NA-Lys$^{ED}$ | 14 |
| NA-Lys$^{PEG}$ | 14 |
| NA-RNaseA$^{ED}$ | 16 |
| NA-RNaseA$^{PEG}$ | 18 |
| NA-CytC$^{ED}$ | 7 |
| NA-CytC$^{PEG}$ | 6 |

Additional TEM Images for Ethylenediamine and (PEO)$_4$-Bis-Amine Cross-Linked Nanoassemblies Transmission electron microscopy (TEM) images were obtained using an JEOL JEM-2000FX instrument operating at 120 kV. Energy-dispersive X-ray spectroscopy (EDX) was obtained with a JEOL JEM-2200FS microscope after cooling the sample in liquid N$_2$.

Enzymatic Degradation (Trypsin Digest) Study

Polymer-protein conjugate solutions and native proteins (lysozyme, RNase A and cytochrome C) were subjected to enzymatic degradation study to evaluate the stealth power of polymeric nanoassemblies to encapsulate and protect the sensitive cargoes from protease mediated cleavage. Sample solutions were prepared with polymer-protein complexes (with final protein concentration of 0.39 mg/mL based on previous protein analysis) in NaHCO$_3$ buffer (pH=8.0). The concentrations of native proteins in each control sample were also kept identical for comparison purpose. After that 10% acetonitrile was added to each sample to denature the protein and incubated at 50° C. for 45 minutes. For RNase A, samples were treated with 15% AcOH and incubated at 90° C. for 4 h. After hydrolysis, samples were freeze-dried and finally added 10% acetonitrile and 90% NaHCO$_3$ buffer of pH 8.0. Finally, all samples were digested with trypsin from porcine pancreas at a ratio of 1:25 (trypsin:protein) at 37° C. for 17 h. After digestion samples were collected by centrifugation and subjected to MALDI-MS analysis. The matrix was prepared with a solvent mixture of acetonitrile, water and trifluoroacetic acid (with a ratio 50:47.5:2.5) containing 10 mg/mL α-cyano-hydroxycinnamic acid. The matrix and digested samples were mixed at 1:1 ratio and spotted on the MALDI target for fragmental analysis.

TABLE 6

Major MS-Digest fragments for Lysozyme, RNase A and Cytochrome C from MALDI-MS analysis

| m/z | Start | End | Sequence |
|---|---|---|---|
| Lysozyme | | | |
| 1045 | 135 | 143 | (K)GTDVQAWIR(G) |
| 1428 | 52 | 63 | (K)FESNFNTQATNR(N) |
| 1676 | 116 | 130 | (K)IVSDGNGMNAWVAWR(N) |
| 1753 | 64 | 79 | (R)NTDGSTDYGILQINSR(W) |
| RNase A | | | |
| 1151 | 1 | 10 | (-)MPAPATTYER(I) |
| 1547 | 85 | 98 | (K)LWSSLTLLGSYKGK(N) |
| 1662 | 1 | 14 | (-)MPAPATTYERIVYK(N) |
| 1685 | 26 | 41 | (R)LEFQDGGVGLTAAQFK(Q) |

TABLE 6-continued

Major MS-Digest fragments for Lysozyme, RNase A and Cytochrome C from MALDI-MS analysis

| m/z | Start | End | Sequence |
|---|---|---|---|
| Cytochrome C | | | |
| 1168 | 29 | 39 | (K)TGPNLHGLFGR(K) |
| 1478 | 89 | 100 | (K)KTEREDLIAYLK(K) |
| 1478 | 90 | 101 | (K)TEREDLIAYLKK(A) |
| 1598 | 40 | 54 | (R)KTGQAPGFTYTDANK(N) |
| 1633 | 10 | 23 | (K)IFVQKCAQCHTVEK(G) |

Assessment of Serum Stability of NA-Lys$^{PEG}$, NA-RNaseA$^{PEG}$ and NA-CytC$^{PEG}$ Nanoassemblies To the stability of nanoassemblies in serum is considered to be an important criterion to perform as an efficient delivery vehicle. The serum stability of the PPCs was performed by monitoring the changes in particle size through DLS. (Mohr, et al. 2014 Langmuir 30, 14954.) All samples were incubated with differential amounts of serum (0%, 10%, 25% and 50%) for 6 h at 37° C. before subjecting to DLS measurements. Conjugates were found to quite stable with negligible shifts in the particle sizes confirming no protein adsorption leading to aggregation and biofouling.

SDS-PAGE for Protein-Polymer Conjugation and Release Studies

30 µL of different samples containing NA-Empty$^{ED}$, NA-Empty$^{PEG}$, NA-Lys$^{ED}$, NA-Lys$^{PEG}$, NA-RNaseA$^{ED}$, NA-RNaseA$^{PEG}$, NA-CytC$^{ED}$ and NA-CytC$^{PEG}$ were mixed with 10 µL of loading buffer (DTT free) and 25 µL of each sample was loaded on acrylamide gel. For release experiment, identical protein-polymer conjugate samples were treated with 10 mM DTT and incubated at 37° C. for 4 h before subjecting to acrylamide gel electrophoresis. To calculate the amount of released protein from each sample, standard curves were generated from the known concentrations of pure protein samples loaded into the gel lanes. The gel image analysis and quantification were performed with Bio-Rad Image Lab™ software.

Release Kinetics of Proteins from the Protein-Polymer Nanoassemblies

To monitor the release kinetics of proteins (lysozyme, RNase A and cytochrome C), 30 µL of NA-Lys$^{ED}$, NA-Lys$^{PEG}$, NA-RNaseA$^{ED}$, NA-RNaseA$^{PEG}$, NA-CytC$^{ED}$ and NA-CytC$^{PEG}$ samples were incubated at 37° C. with requisite amounts of 10 mM DTT for different time intervals. After each incubation time, samples were collected and immediately frozen at −20° C. Finally, all samples were subjected to SDS-PAGE analysis to quantify the amount of released proteins. Encapsulation and release studies with variations in DTT concentrations and crosslinker concentrations were carried out using similar experimental protocols.

Activity Assays

To measure the activity of released proteins from different polymer-protein conjugates, first samples were treated with 10 mM DTT and incubated at 37° C. for 4 h. Identical samples were subjected to 50 µM DTT mimicking extracellular reducing environment and incubated under similar condition.

SpectraMax® M5 spectrophotometer (Molecular Devices) was utilized for evaluating all activities through absorbance and fluorescence measurements.

a. For Lysozyme

The EnzChek® Lysozyme Assay Kit (Thermo-Fisher Scientific) was used to check the lysozyme activity on a substrate based on *Micrococcus lysodeikticus* cell walls which was labeled with fluorescein to such an extent that the fluorescence is quenched. Due to lysozyme's enzymatic activity, the mucopolysaccharide cell walls of the labelled microorganism containing β-(1-4)-glucosidic linkages between N-acetylmuramic acid and N-acetyl-D-glucosamine residues were hydrolysed releasing proportional amount of fluorescein. To perform the assay, 20 μL sample was mixed with 20 μL prepared substrate solution and subjected to fluorescence measurement (Ex/Em: 494/518 nm) over 1 h time period with SpectraMax® M5 spectrophotometer.

b. For RNase A

RNaseAlert® activity kit (Thermo-Fisher Scientific) was used to check the activity of released RNase A for all samples. RNase A cleaves the oligonucleotide substrate of the assay consisting a fluorophore and a quencher present at two extreme ends, thus releasing the fluorophore which can be detected and quantified with a fluorometer. For a typical kinetic experiment, the substrate was mixed with 5 μL test buffer, 35 μL nuclease free water and 10 μL sample (diluted ×10,000 from DTT experiment). 40 μL of the prepared sample mixture was transferred to a black 96-well plate and immediately measured for fluorescence (Ex/Em: 490/520 nm) with SpectraMax® M5 spectrophotometer over a 30 min time course.

c. For Cytochrome C

The peroxidase activity of cytochrome C was determined by examining the catalytic conversion of 2,2'-azino-bis(3-ethylbenzthiazoline-6-sulfonic acid) (ABTS). Cytochrome C catalyzes the reduction of $H_2O_2$ to water which is coupled with one-electron oxidation of chromogenic ABTS forming a brilliant blue-green ABTS radical cation. The assay kinetics can be monitored by observing the changes in absorbance spectra of the radical cation at 418 nm. Before subjecting to activity measurement, DTT treated samples were washed thoroughly with PBS buffer of pH 7.4 to remove DTT and other byproducts. The test solution was prepared by mixing 100 μL sample solution with 400 μL $H_2O_2$ (25 mM) and 500 μL ABTS (1 mg/mL). Absorbance spectra were recorded for all samples at 418 nm for a time course of 5 min using SpectraMax® M5 spectrophotometer.

TABLE 7

Abbreviations used in activity assay plots

| Sample | Details | Sample | Details |
|---|---|---|---|
| Protein_DTT 0.05 mM | Native protein treated with 0.05 mM DTT | NA-Protein$^{PEG}$ 0.05 mM | Protein encapsulated PEGcrosslinked Nanoassemblies treated with 0.05 mMDTT |
| Protein_DTT 10 mM | Native protein treated with 10 mM DTT | NA-Protein$^{ED}$ 10 mM | Protein encapsulated EDcrosslinked Nanoassemblies treated with 10 mMDTT |
| NA-Empty$^{ED}$ | Empty ED-crosslinked nanoassemblies treated with 10 mM DTT | NA-Protein$^{PEG}$ 10 mM | Protein encapsulated PEGcrosslinked Nanoassemblies treated with 10 mMDTT |
| NA-Empty$^{PEG}$ | Empty PEG-crosslinked nanoassemblies treated with 10 mM DTT | Blank | Only phosphate buffer, pH 7.4 |

TABLE 7-continued

Abbreviations used in activity assay plots

| Sample | Details | Sample | Details |
|---|---|---|---|
| NA-ProteinED 0.05 mM | Protein encapsulated ED-crosslinked nanoassemblies treated with 0.05 mMDTT | | |

Circular Dichroism (CD) Spectra

CD spectra of the released and native protein samples were recorded on JASCO J-1500 spectrophotometer. In a typical experiment, NA-protein sample was incubated with requisite amount of DTT for 24 h. After that, the sample was dialyzed against PBS buffer pH 7.4 with a membrane MWCO 20 kDa for 2 days to separate the polymer. Finally, the purified sample was concentrated with Amicon Ultra Centrifugal Filters MWCO 3K and the concentration was measured with Pierce 660 nm Protein Assay Reagent. For recording the spectra, 200 μL protein solution was injected into a quartz cuvette of 1-mm path length, equilibrated at 25° C. for 10 min and scanned from 190 to 250 nm (scan rate: 20 nm/min, interval: 0.2 nm, average of three spectra).

MALDI-MS Spectra for the Released Proteins

MALDI-MS analyses were performed with Bruker Autoflex III time-of-flight mass spectrometer. All mass spectra were acquired in the reflectron mode with an average of 500 laser shots at ~60% optimized power.

Labeling of Proteins with Rhodamine B

To perform the cell-uptake studies, fluorescence-labelled proteins (lysozyme, RNase A and cytochrome C) were prepared with Rhodamine B isothiocyanate (RB). In a typical labelling procedure, proteins (4 mg) were dissolved separately in 2 mL of 0.1 M $NaHCO_3$ buffer (pH 8.5) and stirred for 15 min at 4° C. RB (5 eq. of each protein, 10 mg/mL in DMSO) was added dropwise to each protein solution and stirred at 4° C. for 2 h protected from light. The RB-labelled-proteins were purified by extensive dialysis with 50 mM Tris pH 7.4 and 50 mM NaCl mixture to remove excess RB and concentrated using 3 kDa Amicon Ultra Centrifugal Filters. Protein concentrations in each labelled conjugates were calculated using UV-Vis spectroscopy. The molar ratio of RB and labelled lysozyme, RNase A and cytochrome C were estimated to be 0.62, 0.43 and 0.63, respectively.

All labelled polymer-protein conjugates were prepared with the RB-labelled proteins following the method described under 'Synthesis of polymer-protein nanoassemblies'.

Cell Culture

Human cervical carcinoma (HeLa) cells were cultured in T75 cell culture flask containing Dulbecco's Modified Eagle Medium/Nutrient Mixture F-12 (DMEM/F12) in a humidified incubator with 5% $CO_2$ at 37° C. Culture media was supplemented with 10% fetal bovine serum (FBS), 1% L-glutamine and 1% antibiotic-antimycotic (100 units/mL of penicillin, 100 μg/mL of streptomycin, and 0.25 μg/mL of Amphotericin B).

Cellular Uptake Studies for Protein Delivery and Endosomal Escape

Cell internalization studies were performed with HeLa cells seeded at 100,000 cells/mL in glass-bottomed petri-dishes and cultured for 1 day at 37° C. in a 5% $CO_2$ incubator. Prior to delivery cells were washed three times with PBS buffer and incubated with 1 mL media containing 6 μL polymer-Rhodamine B-protein conjugate or Rhodamine B-protein conjugate (protein concentration 1 mg/mL) at 37° C. for 4 h. After that, cell nucleus was stained with Hoechst 33342 (8 μM) and finally the media was replaced with fresh stock and incubated for another 1 h before subjecting to CLSM analysis. In addition, to study the endosomal escape of the labelled proteins, HeLa cells were incubated with labelled nanoassemblies for 4 and 24 h. After that it was stained with LysoTracker® Green to label endosomes/lysosomes and studied the co-localization of red and green fluorescence channels. Live cell imaging was performed using Nikon Spectral A1+ confocal microscope. Similar procedure was utilized for the cellular uptake studies with DU-145 and 293T cell lines.

Investigation of Cellular Uptake Pathways

Cells were seeded at $1.2 \times 10^5$ cells/mL concentration in 6-well plate and cultured for 1 day at 37° C. in a 5% $CO_2$ incubator. After 24 h, media was replaced with fresh DMEM/F-12 containing different endocytosis inhibitors (EIPA: 100 μM, Nystatin: 30 μM, hyperosmolar sucrose: 0.45 M) and incubated for 1 h. Afterwards media was discarded and treated with different inhibitors containing media with NA-CC$^{PEG}$-Rhodamine conjugates. After 1 h incubation at 37° C. in 5% $CO_2$, media was removed and washed with PBS three times. Cells were then trypsinized and harvested for flow cytometry analysis in BD LSR-Fortessa.

Cell Viability with alamarBlue® Assay

HeLa cells were seeded into 96-well tissue culture plates at a density of 5000 cells/well/100 μL sample and incubated at 37° C. After 24 h, culture media was replaced and cells were treated with different concentrations of protein-polymer conjugates and control protein samples (0.1 mg/mL to 2 mg/mL protein concentration) in 100 μL media. All samples were incubated for 6 h at 37° C., then the media was replaced and incubated for another 66 h at 37° C. Afterwards media was replaced, washed with PBS buffer for three times and each well was treated with 100 μL 10% alamarBlue in media with serum. Finally, samples were incubated for 1 h and subjected to fluorescence measurement with SpectraMax® M5 at 560 nm excitation/590 nm emission wavelength in a black 96-well flat bottomed plate. Cellular viability of the small molecule byproducts were assessed using a similar protocol.

Study of Apoptosis with NA-CytC$^{PEG}$ Nanoassembly

HeLa cells were seeded at 40,000 cells/mL density in glass-bottomed petri-dishes and cultured for 1 day at 37° C. in a 5% $CO_2$ incubator. Cells were washed three times with PBS buffer and incubated with 1 mL media containing NA-CytC$^{PEG}$ conjugate (2 mg/mL) at 37° C. for 4 h. After that, the media was replaced and cells were incubated for another 68 h. To detect the apoptotic cells, each sample was treated with CellEvent™ Caspase-3/7 Red Detection Reagent (10 μM) and hoechst 33342 (8 μM) to stain the nucleus by incubating for 30 min before subjecting to CLSM analysis. The apoptosis assay reagent consists of a DEVD peptide attached to a nucleic acid-binding cy5-dye. When bound with the peptide, the dye becomes intrinsically non-fluorescent as the DEVD peptide retards the DNA-binding ability of the dye. Once caspase-3/7 enzymes are activated in apoptotic cells by the delivery of cytochrome C, the DEVD peptide is cleaved by those and enable the dye to bind to DNA to produce a bright, fluorogenic response. Co-localization of blue (hoechst) and red (cy5) channels was studied to check the nuclei of the apoptotic cells.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A polymer-protein conjugate comprising a protein covalently conjugated to a polymer having the structural formula of:

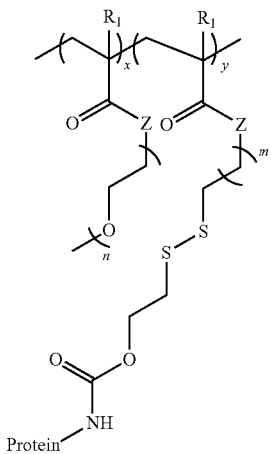

wherein the protein is selected from the group consisting of intracellular proteins bearing at least one lysine residue in their monomeric or aggregated form
wherein each $R_1$ is H, methyl or Br,
Z is O or NH, and each of m, n, x and y is a positive integer,
and the polymer-protein conjugate is formed by one or more reactions between one or more side chain functionalities of the polymer and one or more surface-exposed functional groups of one or more lysine residues of the protein, leading to covalent capture and organization of the polymer around the protein.

2. A nano-assembly comprising the polymer-protein conjugate of claim 1, wherein the polymer is crosslinked forming a crosslinked polymer nextwork and the protein is encapsulated in and covalently conjugated to the crosslinked polymer nextwork; and the crosslinked polymer network is de-crosslinkable thereby tracelessly releasing the protein in its original form, wherein the crosslinker is a diamine.

3. The nano-assembly of claim 2, wherein the crosslinked polymer network is de-crosslinkable in response to a specific microenvironment resulting in degradation of the nano-assembly and release of the protein.

4. The nano-assembly of claim 2, wherein the crosslinked polymer network is decrosslinked inside an intracellular reducing environment, thereby releasing the protein.

5. The nano-assembly of claim 2, wherein the released protein is biologically active.

6. The polymer-protein conjugate of claim 1, wherein R1 is methyl, Z is O, and m is 1.

7. The nano-assembly of claim 2, wherein the diamine crosslinker is ethylenediamine.

* * * * *